US010406089B2

(12) United States Patent
Gebert-Schwarzwaelder et al.

(10) Patent No.: US 10,406,089 B2
(45) Date of Patent: *Sep. 10, 2019

(54) AGENTS FOR DYEING KERATIN FIBRES, CONTAINING AT LEAST ONE DIMERIC, DICATIONIC AZO DYE WITH SPECIAL SUBSTITUTION PATTERN

(71) Applicant: Henkel AG & Co. KGaA, Dusseldorf (DE)

(72) Inventors: Antje Gebert-Schwarzwaelder, Neuss (DE); Helmut Giesa, Meerbusch (DE); Astrid Kroos, Monheim (DE)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,529

(22) PCT Filed: Oct. 14, 2015

(86) PCT No.: PCT/EP2015/073779
§ 371 (c)(1),
(2) Date: May 22, 2017

(87) PCT Pub. No.: WO2016/083015
PCT Pub. Date: Jun. 2, 2016

(65) Prior Publication Data
US 2017/0266093 A1 Sep. 21, 2017

(30) Foreign Application Priority Data

Nov. 25, 2014 (DE) .................. 10 2014 223 936

(51) Int. Cl.
A61Q 5/10 (2006.01)
A61K 8/49 (2006.01)
A61Q 5/06 (2006.01)
A61K 8/22 (2006.01)
A61Q 5/08 (2006.01)
C09B 31/14 (2006.01)

(52) U.S. Cl.
CPC ............... A61K 8/49 (2013.01); A61K 8/22 (2013.01); A61K 8/496 (2013.01); A61K 8/4946 (2013.01); A61Q 5/065 (2013.01); A61Q 5/08 (2013.01); C09B 31/14 (2013.01); A61K 2800/4322 (2013.01)

(58) Field of Classification Search
CPC .......... A61Q 5/065; A61Q 5/08; C09B 44/20; C09B 31/14; A61K 8/49
See application file for complete search history.

(56) References Cited

U.S. PATENT DOCUMENTS 4,562,249 A    12/1985   Schwander et al.
4,563,191 A    1/1986    Hahnke et al.
4,607,071 A    8/1986    Haehnke et al.
7,407,516 B2   8/2008    Vidal
2001/0001333 A1   5/2001   Samain
2004/0200009 A1* 10/2004   Vidal .................... C09B 44/126
                                                        8/405
2004/0244124 A1  12/2004   Plos et al.
2005/0235433 A1  10/2005   Rondeau
2006/0112502 A1  6/2006    Cotteret et al.
2012/0325261 A1  12/2012   Hashimoto et al.
2014/0101868 A1*  4/2014   Hoffmann ............... A61K 8/891
                                                        8/407
2014/0165301 A1*  6/2014   Schweinsberg ........ A61K 8/898
                                                        8/409
2014/0289970 A1  10/2014   Gross et al.

FOREIGN PATENT DOCUMENTS

CA   2303209 A1   3/1999
DE   2822912 A1   11/1979
DE   4128490 A1   3/1993
EP   0531943 A1   3/1993
EP   1609456 A1   12/2005
EP   1483334 B1   7/2007
EP   1448156 B1   8/2007
FR   2915681 A1   11/2008
GB   910121 A     11/1962
GB   1186753 A    4/1970
GB   1189753 A    4/1970
WO   02100369 A2  12/2002

OTHER PUBLICATIONS

STIC Search Report dated Jul. 29, 2017.*
EPO, International Search Report and Written Opinion issued in International Application No. PCT/EP2015/073779, dated Nov. 30, 2015.
EPO, International Search Report and Written Opinion issued in International Application PCT/EP2015/072773, dated Nov. 12, 2015.
Preliminary Amendment for U.S. Application entitled "Agents for Dyeing Keratin Fibers, Containing At Least One Dimeric, Dicationic Azo Dye and At Least One Anionic Surfactant".
Substitute Specification for U.S. Application entitled "Agents for Dyeing Keratin Fibers, Containing At Least One Dimeric, Dicationic Azo Dye and At Least One Anionic Surfactant".
EPO, International Search Report and Written Opinion issued in International Application PCT/EP2015/072774, dated Nov. 23, 2015.
Preliminary Amendment for US. Application entitled "Agents For Dyeing Keratin Fibers, Containing At Least One Dimeric, Dicationic Azo Dye and At Least One Non-Ionic Surfactant".
Substitute Specification for US. Application entitled "Agents For Dyeing Keratin Fibers, Containing At Least One Dimeric, Dicationic Azo Dye and At Least One Non-Ionic Surfactant".
EPO, International Search Report and Written Opinion issued in International Application PCT/EP2015/073775, dated Dec. 1, 2015.
Preliminary Amendment for U.S. Application entitled "Agents for Dyeing Keratin Fibers, Containing At Least One Dimeric, Dicationic Azo Dye and At Least One Anionic and/or Cationic Surfactant".

(Continued)

Primary Examiner — Eisa B Elhilo
(74) Attorney, Agent, or Firm — Lorenz & Kopf, LLP

(57) ABSTRACT

The disclosure relates to agents for dyeing keratin fibers, in particular human hair, containing, in a cosmetic carrier (a) at least one direct dye of formula (I), wherein Het1, Het2 represent cationic heterocycles; R1, R3 respectively represent a substitute which is not hydrogen, and Q represents a grouping of formula (VIII), (IX), or (X).

20 Claims, No Drawings

(56) References Cited

OTHER PUBLICATIONS

Substitute Specification for U.S. Application entitled "Agents for Dyeing Keratin Fibers, Containing At Least One Dimeric, Dicationic Azo Dye and At Least One Anionic and/or Cationic Surfactant".
EPO, International Search Report and Written Opinion issued in International Application No. PCT/EP2015/073776, dated Nov. 30, 2015.
Preliminary Amendment for U.S. Application entitled "Agents for Dyeing Keratin Fibers, Containing At Least One Dimeric, Ring-Bridged Azo Dye".
Substitute Specification for U.S. Application entitled "Agents for Dyeing Keratin Fibers, Containing At Least One Dimeric, Ring-Bridged Azo Dye".
USPTO, Office Action in U.S. Appl. No. 15/528,538 dated Aug. 30, 2017.
USPTO, Office Action in U.S. Appl. No. 15/528,539 dated Aug. 31, 2017.
USPTO, Office Action in U.S. Appl. No. 15/528,530 dated Aug. 31, 2017.
USPTO, Office Action in U.S. Appl. No. 15/528,532 dated Aug. 31, 2017.
STIC Search Report dated Jul. 2, 2017 (U.S. Appl. No. 15/528,538).
STIC Search Report dated Aug. 6, 2017 (U.S. Appl. No. 15/528,539).
STIC Search Report dated Aug. 1, 2017 (U.S. Appl. No. 15/528,530).
STIC Search Report dated Jun. 28, 2017 (U.S. Appl. No. 15/528,532).

\* cited by examiner

AGENTS FOR DYEING KERATIN FIBRES, CONTAINING AT LEAST ONE DIMERIC, DICATIONIC AZO DYE WITH SPECIAL SUBSTITUTION PATTERN

CROSS-REFERENCE TO RELATED APPLICATIONS

This application is a U.S. National-Stage entry under 35 U.S.C. § 371 based on International Application No. PCT/EP2015/073779, filed Oct. 14, 2015, which was published under PCT Article 21(2) and which claims priority to German Application No. 10 2014 223 936.2, filed Nov. 25, 2014, which are all hereby incorporated in their entirety by reference.

TECHNICAL FIELD

The present disclosure relates to agents for colouring keratinic fibers, in particular human hair, which contain (a) at least one dimeric, dicationic azo dye with a particular formula (I).

BACKGROUND

In order to colour keratinic fibers, in general, either direct dyes or oxidation dyes are used. Although intensive colours can be obtained with good fastness properties using oxidation dyes, development of the colour in general occurs by the action of oxidizing agents such as $H_2O_2$, for example, which in some cases can result in damage to the fibers. Furthermore, some oxidation dye precursors or specific mixtures of oxidation dye precursors may have a sensitizing effect on some people with sensitive skin. Direct dyes are applied under kinder conditions. However, they suffer from the disadvantage that the colours frequently do not have satisfactory fastness properties.

The person skilled in the art categorizes direct dyes into different dye classes as a function of the desired colour result. As an example, direct dyes which are known in the art belong to the nitro dye, anthraquinone dye, azo dye, triarylmethane dye or methine dye classes. All of these classes of dyes should comply with a specific specification profile for use in cosmetics. Thus, direct dyes should provide an intensive coloration and have fastness properties which are as good as possible. The resulting colour obtained with direct dyes should be affected by the environment as little as possible, i.e. the dyes should, for example, have good wash fastness, light fastness and rubbing fastness. Chemical actions to which the keratinic fibers could be exposed following the dyeing process (such as permanent waving, for example) should also alter the resulting colour as little as possible.

In order to obtain a lightening effect at the same time as a colour, the direct dyes should, where possible, also be compatible with the oxidizing agents normally employed during a bleaching procedure (for example hydrogen peroxide and/or persulphates).

In order to ultra-lighten dark hair, not only hydrogen peroxide alone, but also a combination of hydrogen peroxide and persulphates (for example ammonium persulphate, potassium persulphate and/or sodium persulphate) is used. If, then, dark hair is ultra-lightened in one step and simultaneously dyed to a bright shade, then the use of a mixture of hydrogen peroxide, persulphates and a direct dye is of advantage. Although the person skilled in the art will be aware of many intensively colouring direct dyes for colouring hair, he will only be aware of a very limited selection of dyes which can tolerate the highly oxidative conditions occurring with a mixture of the oxidizing agents mentioned above without decomposing. In addition, the dyes known in the prior art which are stable to oxidation suffer from severe disadvantages as regards their other fastness properties.

For simultaneous colouring and ultra-lightening of hair, then, there is still a need for dyes with a high stability as regards strong oxidizing agents. Even under these extreme application conditions, these dyes should not lose their positive fastness and colouring properties.

It has been shown that bright and intensive colours can in particular be produced with cationic direct dyes. Cationic dyes are frequently distinguished by a particularly high affinity for keratinic fibers, which can be attributed to the interaction of the positive charges of the dyes with negatively charged structural components of the keratinic fibers. Thus, frequently, particularly intensive colours can be obtained with cationic dyes.

Exemplary representatives of monomeric cationic azo dyes which have been known in the prior art for a long time are Basic Orange 31 (alternative name: 2-[(4-aminophenyl)azo]-1,3-dimethyl-1H-imidazolium chloride, CAS-No. 97404-02-9) and Basic Red 51 (alternative name: 2-[((4-dimethylamino)phenyl)azo]-1,3-dimethyl-1H-imidazolium chloride, CAS-No. 77061-58-6).

Both dyes colour keratinic fibers with an excellent colour intensity in the orange to red range of nuances. There is still a need for direct dyes which are as optimally compatible as possible with these two dyes.

BRIEF SUMMARY

Agents for colouring keratinic fibers, in particular human hair are provided herein. In an exemplary embodiment, an agent for changing the colour of keratinic fibers comprises, in a cosmetic support,
(a) at least one direct dye with formula (I),

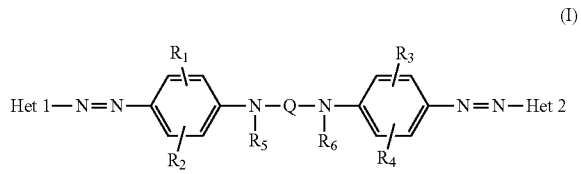

wherein
Het1, Het2 independently of each other represent one of the structures (II), (III), (IV), (V), (VI) or (VII),

-continued

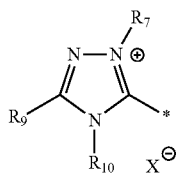
(IV)

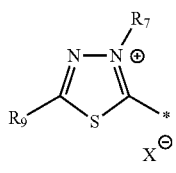
(V)

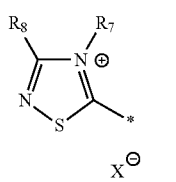
(VI)

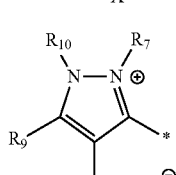
(VII)

R1, R3 independently of each other represent a $C_1$-$C_6$ alkyl group, a halogen atom from the group chlorine, bromine, fluorine or iodine, a $C_1$-$C_6$ alkoxy group or a nitro group, R2, R4 independently of each other represent a hydrogen atom, a $C_1$-$C_6$ alkyl group, a halogen atom from the group chlorine, bromine, fluorine or iodine, a $C_1$-$C_6$ alkoxy group or a nitro group, R5, R6 independently of each other represent a hydrogen atom, a $C_1$-$C_6$ alkyl group or a $C_2$-$C_6$ alkenyl group, Q represents a group with formula (VIII), (IX) or (X),

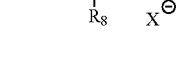

* —(CH$_2$)$n$-*  (VIII)

* —(CH$_2$)$m$-O—(CH$_2$)$p$-*  (IX)

* —(CH$_2$)$m$-O—(CH$_2$)$p$-O—(CH$_2$)$q$-*  (X)

n represents a whole number from 3 to 6, m, p, q each independently of each other represent the numbers 2 or 3, R7, R10 each independently of each other represent a $C_1$-$C_6$ alkyl group or a $C_2$-$C_6$ alkenyl group, R8, R9 each independently of each other represent a hydrogen atom, a $C_1$-$C_6$ alkyl group, a halogen atom from the group chlorine, bromine, fluorine or iodine, a $C_1$-$C_6$ alkoxy group or a nitro group, X— represents a physiologically acceptable anion, preferably from the group chloride, bromide, iodide, methyl sulphate, methyl sulphonate, p-toluenesulphonate, acetate, hydrogen sulphate, ½ sulphate or ½ tetrachlorozincate.

DETAILED DESCRIPTION

The following detailed description is merely exemplary in nature and is not intended to limit the present disclosure or the application and uses of the subject matter as described herein. Furthermore, there is no intention to be bound by any theory presented in the preceding background or the following detailed description.

The object of the present application is thus to provide colorants for keratinic fibers, in particular human hair which, as regards the depth of colour and the fastness properties such as, for example, light, rubbing and wash fastness, as well as perspiration and cold wave fastness, exhibit good technical properties as regards application. In the case of simultaneous application with oxidation dyes and/or oxidizing agents, the direct dyes should exhibit a high stability to hydrogen peroxide and other oxidizing agents and not lose its positive fastness and colour properties. In addition, colours which are as bright and intensive as possible should be obtained.

Furthermore, the dyes mentioned above should also be particularly compatible with the cationic azo dyes Basic Orange 31 and Basic Red 51.

It has now been discovered that the application of dimeric, dicationic azo dyes with general formula (I) to keratinic fibers results in intensive and bright colours. Surprisingly, the direct dyes with general formula (I) also exhibit a high stability as regards oxidizing agents. In this manner, by simultaneously using at least one dye with formula (I), hydrogen peroxide and a persulphate salt, simultaneous lightening (bleaching) and colouring is possible.

In a first aspect, the present disclosure provides an agent for changing the colour of keratinic fibers, in particular human hair, containing, in a cosmetic support (a), at least one direct dye with formula (I), wherein

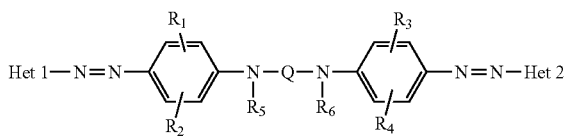
(I)

Het1, Het2 independently of each other represent one of the structures (II), (III), (IV), (V), (VI) or (VII),

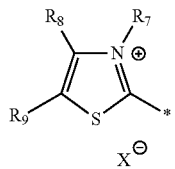
(II)

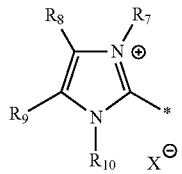
(III)

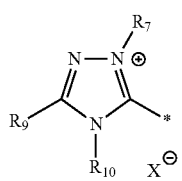
(IV)

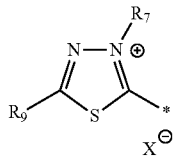

(V)

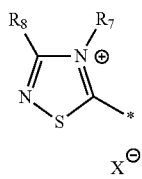

(VI)

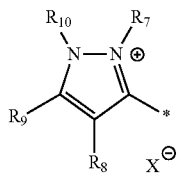

(VII)

R1, R3 independently of each other represent a $C_1$-$C_6$ alkyl group, a halogen atom from the group chlorine, bromine, fluorine or iodine, a $C_1$-$C_6$ alkoxy group or a nitro group, R2, R4 independently of each other represent a hydrogen atom, a $C_1$-$C_6$ alkyl group, a halogen atom from the group chlorine, bromine, fluorine or iodine, a $C_1$-$C_6$ alkoxy group or a nitro group, R5, R6 independently of each other represent a hydrogen atom, a $C_1$-$C_6$ alkyl group or a $C_2$-$C_6$ alkenyl group, Q represents a group with formula (VIII), (IX) or (X), $$* \text{—}(CH_2)n\text{-}* \quad (VIII)$$

$$* \text{—}(CH_2)m\text{-O—}(CH_2)p\text{-}* \quad (IX)$$

$$* \text{—}(CH_2)m\text{-O—}(CH_2)p\text{-O—}(CH_2)q\text{-}* \quad (X)$$

n represents a whole number from 3 to 6, m, p, q each independently of each other represent the numbers 2 or 3, R7, R10 each independently of each other represent a $C_1$-$C_6$ alkyl group or a $C_2$-$C_6$ alkenyl group, R8, R9 each independently of each other represent a hydrogen atom, a $C_1$-$C_6$ alkyl group, a halogen atom from the group chlorine, bromine, fluorine or iodine, a $C_1$-$C_6$ alkoxy group or a nitro group, X— represents a physiologically acceptable anion, preferably from the group chloride, bromide, iodide, methyl sulphate, methyl sulphonate, p-toluenesulphonate, acetate, hydrogen sulphate, ½ sulphate or ½ tetrachlorozincate.

The term "keratinic fibers", "keratin-containing fibers" or "keratin fibers" should be understood to mean fur, wool, feathers and in particular human hair. Although the agent in accordance with an exemplary embodiment of the present disclosure is primarily intended for lightening keratinic fibers, in principle, an application to other fields is not excluded.

The term "changing the colour of keratinic fibers" as used in the disclosure encompasses every form of changing the colour of the fibers. In particular, colour changes involved in "tinting", "bleaching", "cool toning", "oxidative colour" "semipermanent colour", "permanent colour" as well as "temporary colour" are included. The colour changes in accordance with an exemplary embodiment of the present disclosure, which produce a brighter colour result compared with the initial colour, such as, for example, bleaching and colouring, are explicitly included. The term "bleaching and colouring" should be understood to mean the simultaneous lightening and colouring of the keratinic fibers, which can be achieved by the simultaneous use of oxidizing agents and dye in the colour changing agent.

The agents in accordance with an exemplary embodiment of the present disclosure contain the direct dyes with formula (I) in a cosmetic support. This cosmetic support is preferably aqueous, alcoholic or hydroalcoholic. For the purposes of the treatment of hair, supports such as creams, emulsions, gels or even foaming solutions containing surfactants such as shampoos, foaming aerosols or other preparations which are suitable for use on the hair are suitable. It is also possible, however, for the purposes of storage, to prepare a powdered formulation or a formulation in tablet form. This is then mixed prior to use with an aqueous solvent or with organic solvents or with mixtures of water and organic solvents in order to obtain the ready-to-use mixture. In the context of the disclosure, an aqueous support contains at least about 40% by weight, in particular at least about 50% by weight of water. In the context of the present disclosure, hydroalcoholic supports should be understood to be aqueous compositions containing about 3% to about 70% by weight of a $C_1$-$C_4$ alcohol, in particular ethanol or isopropanol. The agent in accordance with an exemplary embodiment of the present disclosure may additionally contain other organic solvents such as, for example, 4-methoxybutanol, ethyldiglycol, 1,2-propyleneglycol, n-propanol, n-butanol, n-butyleneglycol, glycerine, diethyleneglycol monoethylether, and diethyleneglycol mono-n-butylether. All water-soluble organic solvents are preferred. Preferred agents in accordance with an exemplary embodiment of the present disclosure are characterized in that they additionally contain a non-aqueous solvent, wherein preferred agents in accordance with the present disclosure contain the solvent in a concentration of about 0.1% to about 30% by weight, preferably in a concentration of about 1% to about 20% by weight, more particularly preferably in a concentration of about 2% to about 10% by weight, respectively with respect to the agent.

The agents in accordance with an exemplary embodiment of the present disclosure contain at least one direct dye with formula (I) as the essential ingredient (a).

The substituents R1 to R10 of the compounds with formula (I) will now be defined by way of example: examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl residues. Examples of a $C_2$-$C_6$ alkenyl group are vinyl, allyl, but-2-enyl, but-3-enyl as well as isobutenyl; preferred $C_2$-$C_6$ alkenyl residues are vinyl and allyl. Halogen atoms are selected from the group chlorine, bromine, fluorine and/or iodine; in this respect, chlorine and bromine are particularly preferred. Examples of a $C_1$-$C_6$ alkoxy group which may be mentioned are methoxy, ethoxy and propoxy groups. The term "nitro group" should be understood to mean a —$NO_2$ group.

Every direct dye with formula (I) carries two cationic, heterocyclic end groups Het1 and Het2 which, independently of each other, are selected from the groups with formulae (II) to (VII):

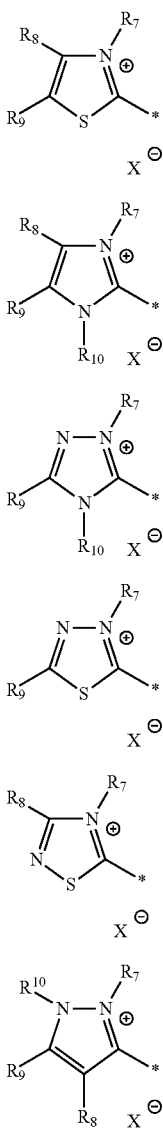

Formula (II) represents a cationic thiazolium end group.

Formula (III) represents a cationic imidazolium end group.

Formula (IV) represents a cationic 1,2,4-triazolium end group.

Formula (V) represents a cationic 1,3,4-thiadiazolium end group.

Formula (VI) represents a cationic 1,2,4-thiadiazolium end group.

Formula (VII) represents a cationic pyrazolium end group.

An asterisk in formulae (II) to (VII) marks a position which is a bonding site for the heterocyclic end group Het1 or Het2 with the azo group in formula (I).

The heterocyclic end groups Het1 and Het2 in the dyes with formula (I) may be the same or different. Purer colours are obtained when Het1 and Het2 are the same in a dye with formula (I).

The absorption spectrum of the dye and thus also the colour of the dye can be altered by selecting different end groups Het1 and Het2.

When intensive colours in the violet or blue-violet region are desired, advantageously, Het1 and Het2 represent heterocyclic end groups with formula (II).

If brilliant colours in the red region are wanted, however, Het1 and Het2 are preferably selected from the heterocyclic end groups with formulae (III) and/or (IV).

Furthermore, with dyes with formula (I), in which Het1 and Het2 represent a group selected from formulae (II), IIII) and (IV), particularly pure and bright shades are obtained. For this reason, particularly preferably, the agent (a) in accordance with an exemplary embodiment of the present disclosure contains at least one direct dye with general formula (I), in which Het1, Het2 independently of each other represent one of the structures (II), (III) or (IV).

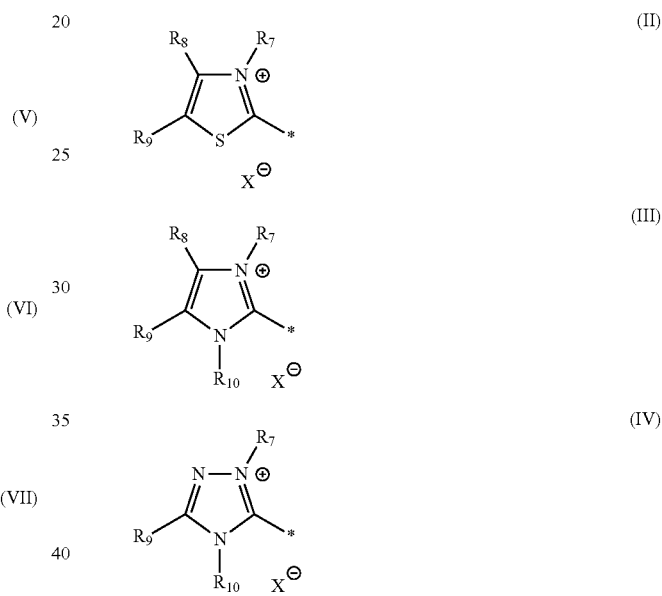

In a particularly preferred embodiment, an agent in accordance with the present disclosure is characterized in that it contains (a) at least one direct dye with general formula (I), in which Het1, Het2 independently of each other respectively represent one of the structures (II), (III) or (IV):

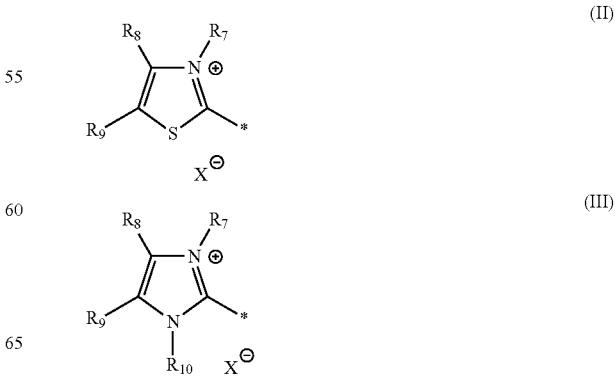

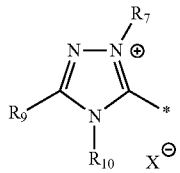
(IV)

The residues R1 to R4 represent the substituents on the two phenyl rings of the direct dye with formula (I).

In this regard, R1 and R3, independently of each other, may represent a $C_1$-$C_6$ alkyl group, a halogen atom from the group chlorine, bromine, fluorine or iodine, a $C_1$-$C_6$ alkoxy group or a nitro group. In principle, R1 and R3 in the dye with formula (I) may be the same or different. However, preferably, R1 and R3 are the same in every dye with formula (I).

The residues R2 and R4 may, independently of each other represent a hydrogen atom, a $C_1$-$C_6$ alkyl group, a halogen atom from the group chlorine, bromine, fluorine or iodine, a $C_1$-$C_6$ alkoxy group or a nitro group. In principle, R2 and R4 in the dye with formula (I) may be the same or different. However, preferably, in every dye with formula (I), R2 and R4 are the same.

Surprisingly, it has been shown that the presence of at least one substituent on each of the two phenyl rings of a dye with formula (I) has an extremely essential influence on the oxidation stability of the dye.

If a dimeric azo dye with the principal construction of formula (I) but, however, which is unsubstituted on the phenyl ring (R1 and R4 are both hydrogen) is bleached in combination with hydrogen peroxide and persulphate salts on keratinic fibers, then the keratinic fibers can only be coloured in pale nuances.

If, however, for the lightening colouring, a dye with formula (I) in accordance with an exemplary embodiment of the present disclosure (with R1 and R3 not being hydrogen) is used in combination with hydrogen peroxide and persulphate salts, then the intensity of the colour is significantly more intensive.

In other words, the oxidation stability of a dye with the general configuration of formula (I) is enhanced by introducing at least one substituent at each of the two phenyl rings of the dye. For this reason, neither of the two residues R1 and R3 can represent a hydrogen atom.

A particularly great increase in the oxidation stability was observed for dyes with general formula (I) in which the residues R1 and R3, independently of each other represent a $C_1$-$C_6$ alkyl group or a $C_1$-$C_6$ alkoxy group.

Particularly preferably, R1 and R3, independently of each other represent a $C_1$-$C_6$ alkyl group.

Yet more particularly preferably, R2 and R4 both represent a hydrogen atom.

In a further particularly preferably embodiment, an agent in accordance with the present disclosure is therefor characterized in that it contains (a) at least one direct dye with general formula (I), in which
R1, R3 independently of each other represent a $C_1$-$C_6$ alkyl group or a $C_1$-$C_6$ alkoxy group,
R2, R4 both represent a hydrogen atom.

Furthermore, the direct dyes with general formula (I) carry the residues R5 and R6. R5 and R6 may, independently of each other, represent a hydrogen atom, a $C_1$-$C_6$ alkyl group or a $C_2$-$C_6$ alkenyl group. Particularly preferably, R5 and R6 independently of each other represent hydrogen or a $C_1$-$C_6$ alkyl group, in particular a methyl group or an ethyl group. R5 and R6 may be the same or different; preferably, R5 and R6 are the same.

In a particularly preferred embodiment, an agent in accordance with the present disclosure is thus characterized in that it contains (a) at least one direct dye with general formula (I), in which
R5, R6 independently of each other represent hydrogen or a $C_1$-$C_6$ alkyl group.

The heterocyclic end groups Het1 and Het2 with formulae (II) to (VII) carry the residues R7, R8, R9 and/or R10.

The residues R7 and R10 are respectively bonded to the nitrogen atom of the heterocycles Het1 and Het2. In this regard, the residues R7 and R10 each independently of each other represents a $C_1$-$C_6$ alkyl group or a $C_2$-$C_6$ alkenyl group. Preferably, R7 and R10 each independently of each other represent a methyl group or an ethyl group.

The residues R8 and R9 may each independently of each other represent a hydrogen atom, a $C_1$-$C_6$ alkyl group, a halogen atom from the group chlorine, bromine, fluorine or iodine, a $C_1$-$C_6$ alkoxy group or a nitro group. Preferably, R8 and R9 both represent a hydrogen atom.

In a further particularly preferred embodiment, an agent in accordance with the present disclosure is thus characterized in that it contains (a) at least one direct dye with general formula (I), in which
R7, R10 each independently of each other represent a methyl group or an ethyl group,
R8, R9 represents a hydrogen atom.

The group Q is a structural unit which bonds the two monopositively charged chromophores of the dye to form dicationic dimers. Q represents a group with formula (VIII), (IX) or (X):

* —(CH$_2$)n-*  (VIII)

* —(CH$_2$)m-O—(CH$_2$)p-*  (IX)

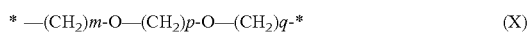
* —(CH$_2$)m-O—(CH$_2$)p-O—(CH$_2$)q-*  (X)

n represents a whole number from 3 to 6,
m, p, q each independently of each other represent the numbers 2 or 3, and the two positions marked with an asterisk herein represent respective bonding positions to the two N atoms of formula (I).

Surprisingly, with the aim of obtaining an intensive colour result, it has transpired in the present disclosure that the binding group Q, which bonds the two individual chromophores together, has a chain length of at least 3 atoms.

For this reason, n in formula (VIII) represents a whole number of at least 3. The binding group Q with formula (VIII) therefore comprises at least 3 C atoms (i.e. herein, the group has a minimum length of —CH$_2$—CH$_2$—CH$_2$—).

In formula (IX), m and p respectively represent a whole number of at least 2, so that this binding group has an overall chain length of at least 5 C and O atoms (i.e. herein, the group has a minimum length of —CH$_2$—CH$_2$—O—CH$_2$—CH$_2$—).

In formula (X), m, p and q respectively represent a whole number of at least 2, so that in an analogous manner, this binding group has a chain length of at least 8 C and O atoms (i.e. herein, the group has a minimum length of —CH$_2$—CH$_2$—O—CH$_2$—CH$_2$—O—CH$_2$—CH$_2$—).

In the context of comparative tests, it has been shown that dimeric azo dyes of the principal type with formula (I) which, however, have a non-inventive linker group Q with a length of only 2 C atoms, have extremely poor colour take-up properties on the keratinic fibers.

While intensive colours can be obtained with the dyes with formula (I) in accordance with an exemplary embodiment of the present disclosure, colours with analogous dimeric dyes which are bonded via a shorter group Q with a chain length of only 2 C atoms result in practically no colour take-up of the keratinic fibers.

Without wishing to be bound by any particular theory, it is possible that a rigid geometry associated with the short linker chain Q, and thus a necessarily unfavourable spatial conformation of the dye, could compromise the diffusion of the short-chained dimeric dyes into the keratinic fibers.

Within the group Q with formulae (VIII), (IX) and (X), the best colour results and the most intensive colours can be obtained with the group with formula (VIII).

In a particularly preferred embodiment, an agent in accordance with the present disclosure is characterized in that it contains (a) at least one direct dye with general formula (I), in which Q represents a group with formula (VIII),

$$* —(CH_2)n-*  \quad\quad (VIII)$$

and n represents a whole number from 3 to 6.

In a specifically particularly preferred embodiment, an agent in accordance with the present disclosure is characterized in that it contains (a) at least one direct dye with general formula (I), in which Q represents a group with formula (VIII),

$$* —(CH_2)n-*  \quad\quad (VIII)$$

and n represents the number 3.

The dyes in accordance with an exemplary embodiment of the present disclosure with formula (I) are dimeric azo dyes which carry a double positive charge. The two positive charges are neutralized by the anionic counter-ion X, the dicationic organic portion herein is responsible for the colour of the keratinic fibers. The counter-ions X act only to provide electrical neutrality, and so the exact nature of the counter-ions X does not play an essential role in obtaining the desired colour result. Because the dye is introduced into a cosmetic substance, the counter-ion X must be physiologically acceptable. "Physiologically acceptable" in this context means suitable for use in a cosmetic substance (i.e. for application to human hair and human skin). "X" is a physiologically acceptable anion, preferably from the group chloride, bromide, iodide, methyl sulphate, methyl sulphonate, p-toluenesulphonate, acetate, hydrogen sulphate, ½ sulphate or ½ tetrachlorozincate.

The term "chloride" should be understood to mean the anion $Cl^-$. The term "bromide" should be understood to mean the anion $Br^-$. The term "iodide" should be understood to mean the anion $I^-$. The term "methyl sulphate" should be understood to mean the anion $H_3COSO_4^-$.

The term "methyl sulphonate" should be understood to mean the anion $H_3CSO_3^-$. The term "p-toluenesulphonate" should be understood to mean the anion $H_3C(C_6H_4)SO_3^-$. The term "acetate" should be understood to mean the anion $H_3CCOO^-$. The term "hydrogen sulphate" should be understood to mean the anion $HSO_4^-$.

The term "½ sulphate" should be understood to mean a half equivalent of the doubly negatively charged anion $SO_4^{2-}$. The term "½ tetrachlorozincate" should be understood to mean a half equivalent of the doubly negatively charged anion $ZnCl_4^{2-}$. Thus, with the sulphate and tetrachlorozincate, it is also possible and inventive for the dicationic dye with formula (I) to be neutralized by a $SO_4^{2-}$ ion or by a $ZnCl_4^{2-}$ ion.

In summary, highly particularly preferred agents for changing the colour of keratinic fibers are characterized in that they contain, in a cosmetic support, (a) at least one direct dye with formula (1a),

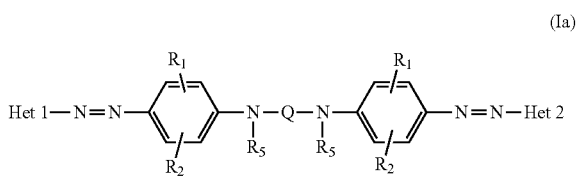

wherein

Het1 represents one of the structures (II), (III) or (IV),

R1 represents a $C_1$-$C_6$ alkyl group, a $C_1$-$C_6$ alkoxy group,

R2 represents hydrogen,

R5 represent hydrogen or a $C_1$-$C_6$ alkyl group

Q represents a group with formula (VIII)

$$* —(CH_2)n-* \quad\quad (VIII)$$

n represents a whole number from 3 to 6,

R7, R10 independently of each other represent a $C_1$-$C_6$ alkyl group,

R8, R9 represent hydrogen,

X— represents a physiologically acceptable anion, preferably from the group chloride, bromide, iodide, methyl sulphate, methyl sulphonate, p-toluenesulphonate, acetate, hydrogen sulphate, ½ sulphate or ½ tetrachlorozincate.

In a further preferred embodiment, an agent for colouring keratinous fibers is characterized in that it contains at least one compound with general formula (I) which is selected from 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts

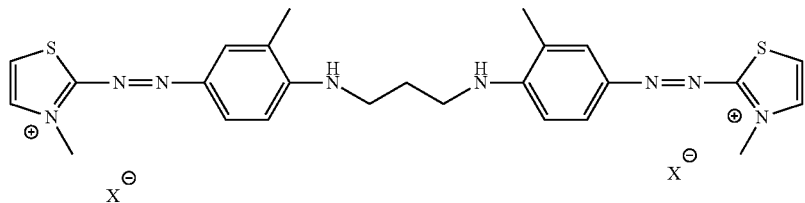

3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts

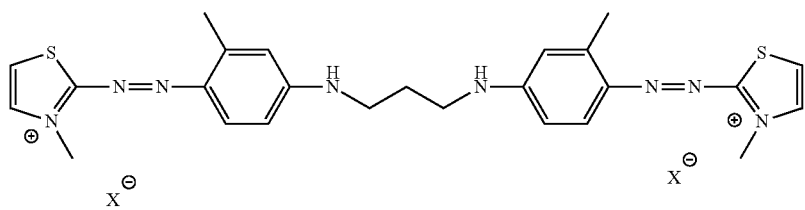

3-methyl-2-[2-(3-methyl-4-{[4-({2-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts

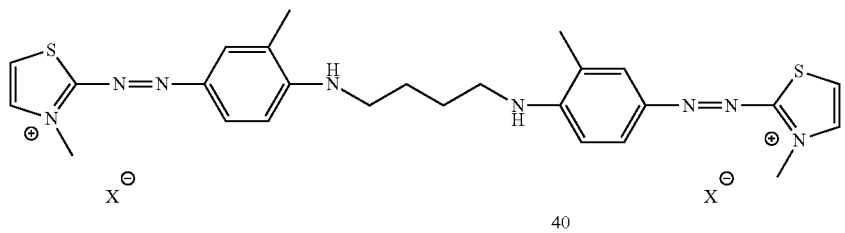

3-methyl-2-[2-(2-methyl-4-{[4-({3-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts

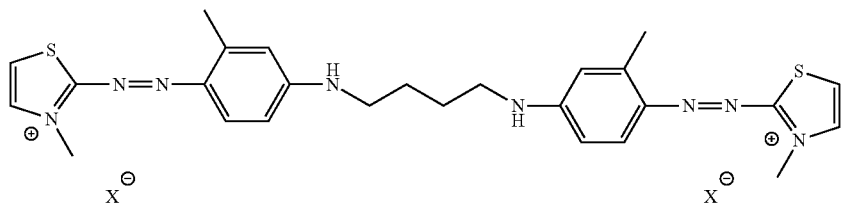

3-methyl-2-[2-(3-methyl-4-{[5-({2-methyl-4-[2-(3-methyl-1,3-thiazol-3-ium-2-yl)diazen-1-yl]phenyl}amino)pentyl]amino}phenyl)diazen-1-yl]-1,3-thiazol-3-ium salts

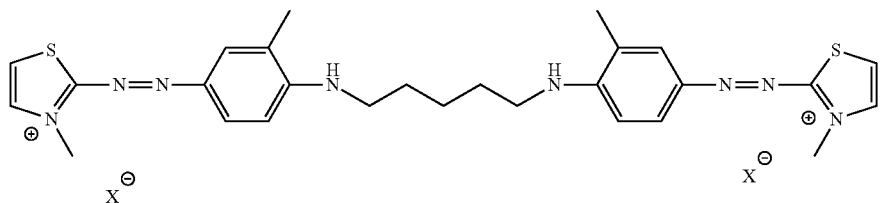

3-methyl-2-[2-(2-methyl-4-{[5-({3-methyl-4-[2-(3-methyl-1,3-thiazol-3-ium-2-yl)diazen-1-yl]phenyl}amino)pentyl]amino}phenyl)diazen-1-yl]-1,3-thiazol-3-ium salts

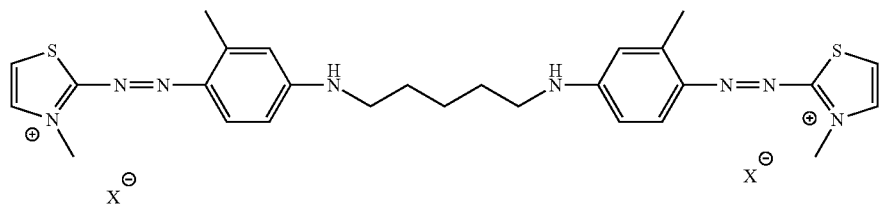

3-methyl-2-(2-{3-methyl-4-[methyl({3-[methyl({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts

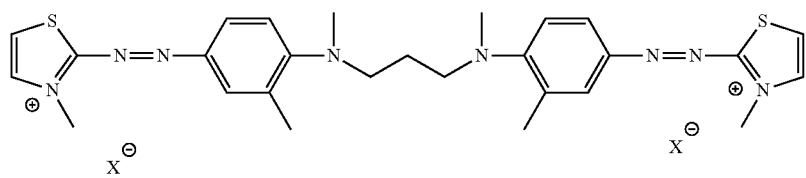

3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

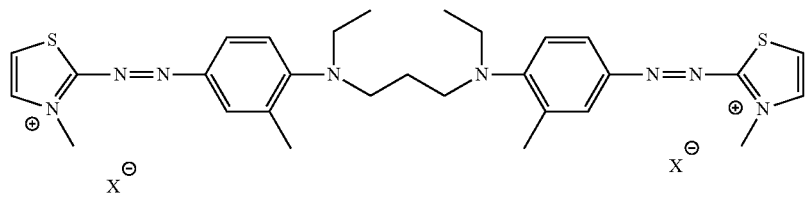

3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

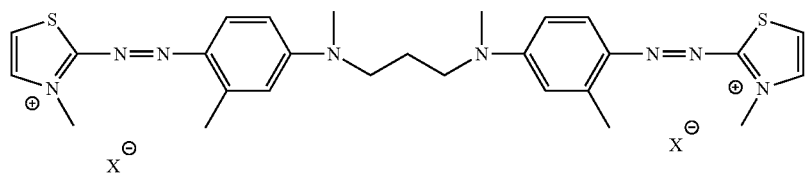

3-methyl-2-(2-{2-methyl-4-[ethyl({3-[ethyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

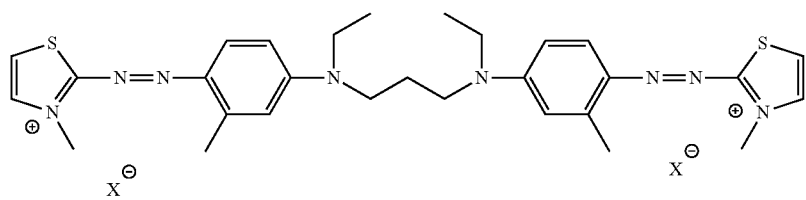

3-methyl-2-(2-{3-methyl-4-[methyl({4-[methyl({2-methyl-4-[2-(3-methyl-1,3-thiazol-3-ium-2-yl)diazen-1-yl]phenyl})amino]butyl})amino]phenyl})diazen-1-yl)-1,3-thiazol-3-ium salts

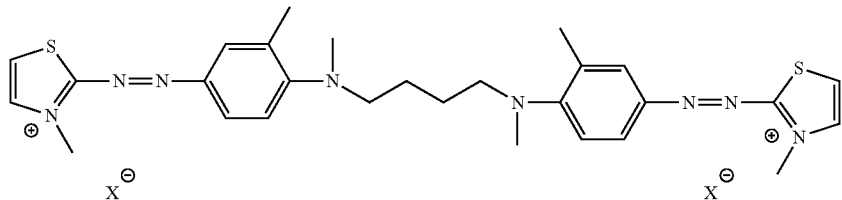

3-methyl-2-(2-{2-methyl-4-[methyl({4-[methyl({3-methyl-4-[2-(3-methyl-1,3-thiazol-3-ium-2-yl)diazen-1-yl]phenyl})amino]butyl})amino]phenyl}diazen-1-yl)-1,3-thiazol-3-ium salts

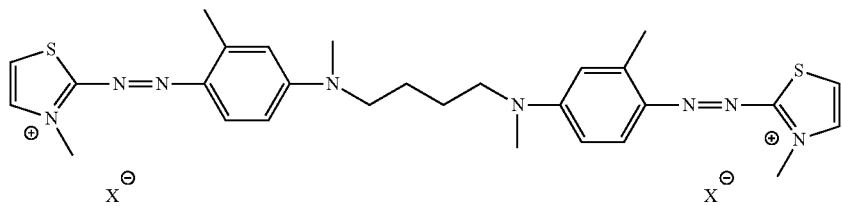

3-methyl-2-(2-{3-methyl-4-[methyl({5-[methyl({2-methyl-4-[2-(3-methyl-1,3-thiazol-3-ium-2-yl)diazen-1-yl]phenyl})amino]pentyl})amino]phenyl}diazen-1-yl)-1,3-thiazol-3-ium salts

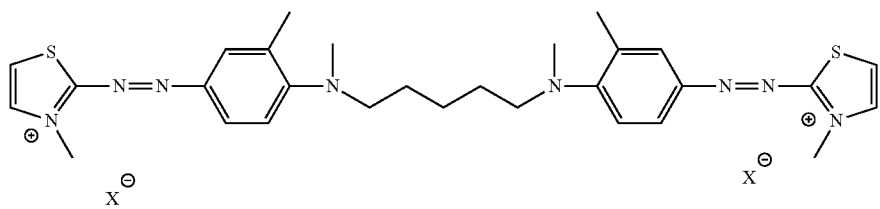

3-methyl-2-(2-{2-methyl-4-[methyl({5-[methyl({3-methyl-4-[2-(3-methyl-1,3-thiazol-3-ium-2-yl)diazen-1-yl]phenyl})amino]pentyl})amino]phenyl}diazen-1-yl)-1,3-thiazol-3-ium salts

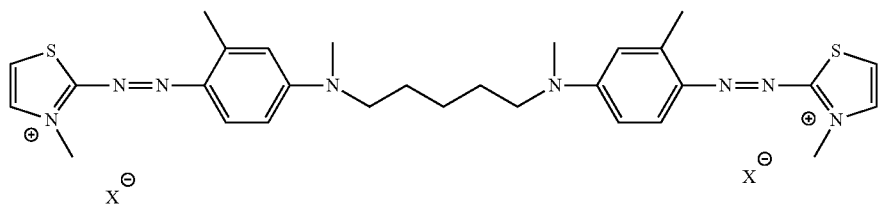

2-[2-(3-methoxy-4-{[3-({2-methoxy-4-[2-(3-methyl-1,3-thiazol-3-ium-2-yl)diazen-1-yl]phenyl}amino)propyl]amino}phenyl)diazen-1-yl]-3-methyl-1,3-thiazol-3-ium salts

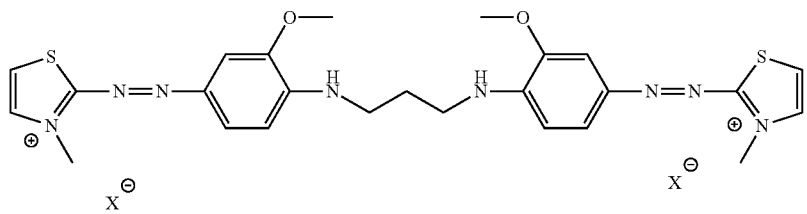

2-[2-(3-methoxy-4-{[4-({3-methoxy-4-[2-(3-methyl-1,3-thiazol-3-ium-2-yl)diazen-1-yl]phenyl}amino)propyl]amino}phenyl)diazen-1-yl]-3-methyl-1,3-thiazol-3-ium salts

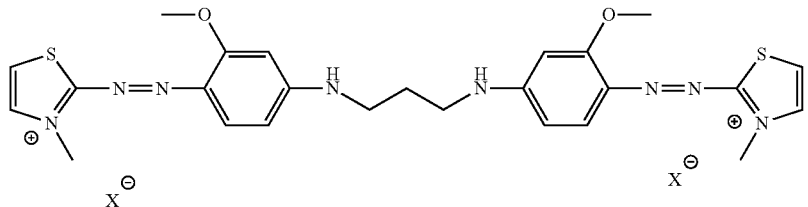

2-[2-(3-methoxy-4-{[4-({2-methoxy-4-[2-(3-methyl-1,3-thiazol-3-ium-2-yl)diazen-1-yl]phenyl}amino)butyl]amino}phenyl)diazen-1-yl]-3-methyl-1,3-thiazol-3-ium salts

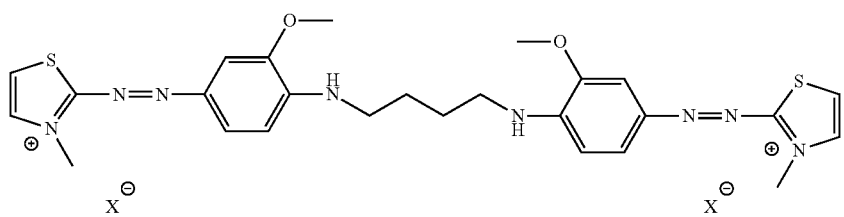

2-[2-(2-methoxy-4-{[4-({3-methoxy-4-[2-(3-methyl-1,3-thiazol-3-ium-2-yl)diazen-1-yl]phenyl}amino)butyl]amino}phenyl)diazen-1-yl]-3-methyl-1,3-thiazol-3-ium salts

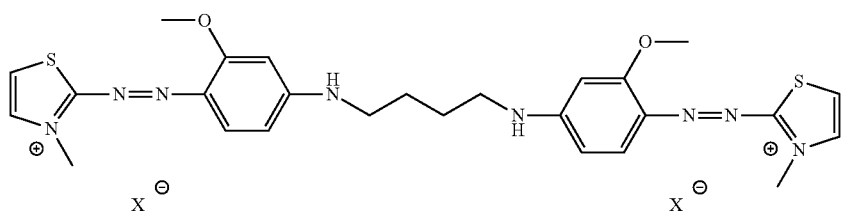

2-[2-(3-methoxy-4-{[5-({2-methoxy-4-[2-(3-methyl-1,3-thiazol-3-ium-2-yl)diazen-1-yl]phenyl}amino)pentyl]amino}phenyl)diazen-1-yl]-3-methyl-1,3-thiazol-3-ium salts

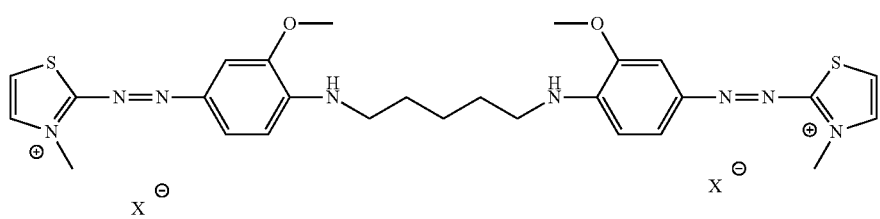

2-[2-(2-methoxy-4-{[5-({3-methoxy-4-[2-(3-methyl-1,3-thiazol-3-ium-2-yl)diazen-1-yl]phenyl}amino)pentyl]amino}phenyl)diazen-1-yl]-3-methyl-1,3-thiazol-3-ium salts

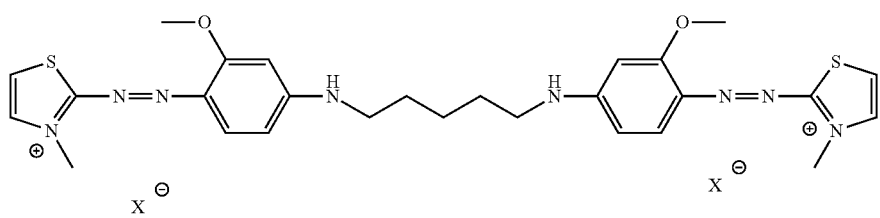

2-[2-(3-methoxy-4-{[3-({2-methoxy-4-[2-(3-methyl-1,3-thiazol-3-ium-2-yl)diazen-1-yl]phenyl}(methyl)amino)propyl](methyl)amino}phenyl)diazen-1-yl]-3-methyl-1,3-thiazol-3-ium salts

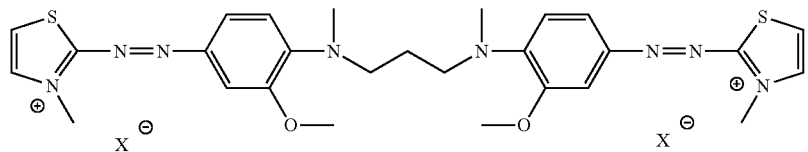

2-[2-(2-methoxy-4-{[3-({3-methoxy-4-[2-(3-methyl-1,3-thiazol-3-ium-2-yl)diazen-1-yl]phenyl}(methyl)amino)propyl](methyl)amino}phenyl)diazen-1-yl]-3-methyl-1,3-thiazol-3-ium salts

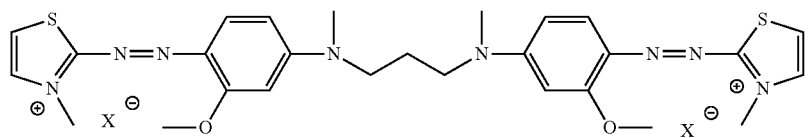

2-[2-(3-methoxy-4-{[4-({2-methoxy-4-[2-(3-methyl-1,3-thiazol-3-ium-2-yl)diazen-1-yl]phenyl}(methyl)amino)butyl](methyl)amino}phenyl)diazen-1-yl]-3-methyl-1,3-thiazol-3-ium salts

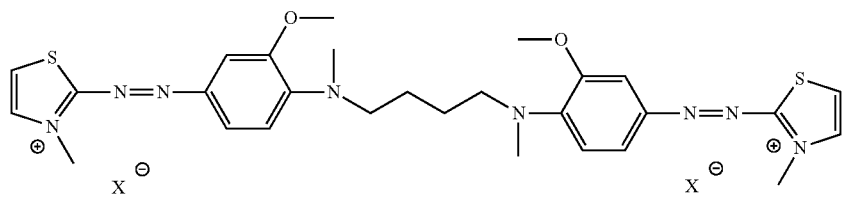

2-[2-(2-methoxy-4-{[4-({3-methoxy-4-[2-(3-methyl-1,3-thiazol-3-ium-2-yl)diazen-1-yl]phenyl}(methyl)amino)butyl](methyl)amino}phenyl)diazen-1-yl]-3-methyl-1,3-thiazol-3-ium salts

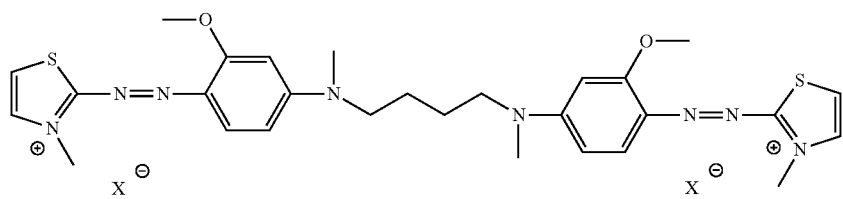

2-[2-(3-methoxy-4-{[5-({2-methoxy-4-[2-(3-methyl-1,3-thiazol-3-ium-2-yl)diazen-1-yl]phenyl}(methyl)amino)pentyl](methyl)amino}phenyl)diazen-1-yl]-3-methyl-1,3-thiazol-3-ium salts

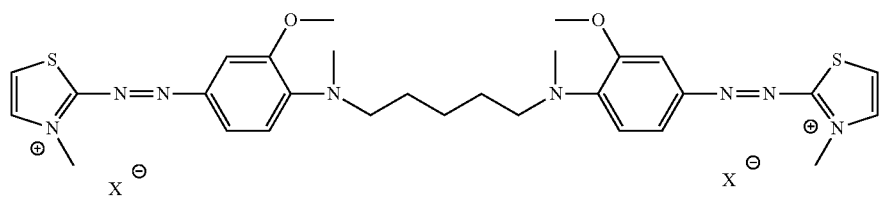

2-[2-(2-methoxy-4-{[5-({3-methoxy-4-[2-(3-methyl-1,3-thiazol-3-ium-2-yl)diazen-1-yl]phenyl}(methyl)amino)pentyl](methyl)amino}phenyl)diazen-1-yl]-3-methyl-1,3-thiazol-3-ium salts

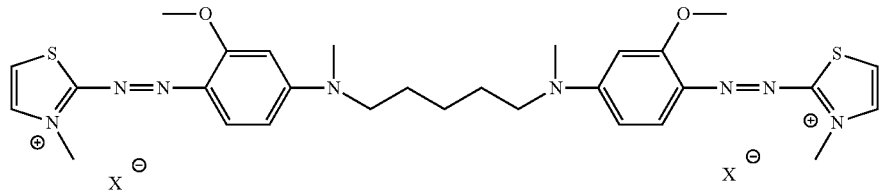

5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium salts

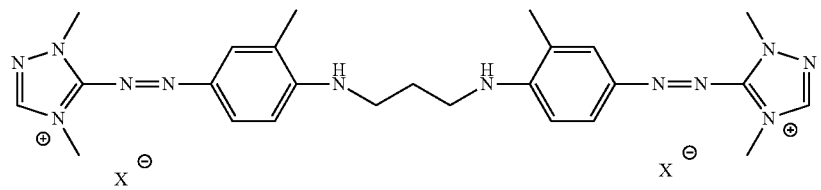

5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium salts

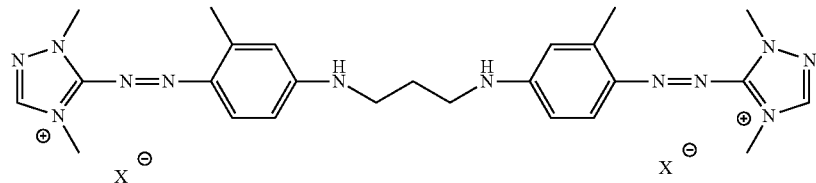

5-[2-(4-{[4-({4-[2-(1,4-dimethyl-1H-1,2,4-triazol-4-ium-5-yl)diazen-1-yl]-2-methylphenyl}amino)butyl]amino}-3-methylphenyl)diazen-1-yl]-1,4-dimethyl-1H-1,2,4-triazol-4-ium salts

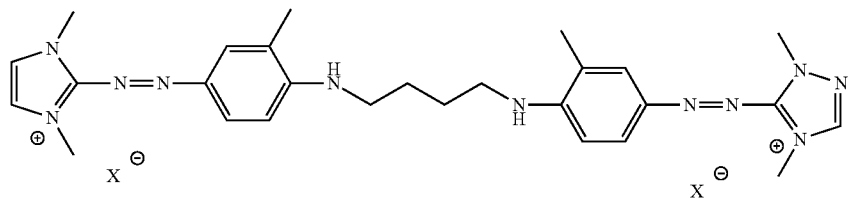

5-[2-(4-{[4-({4-[2-(1,4-dimethyl-1H-1,2,4-triazol-4-ium-5-yl)diazen-1-yl]-3-methylphenyl}amino)butyl]amino}-2-methylphenyl)diazen-1-yl]-1,4-dimethyl-1H-1,2,4-triazol-4-ium salts

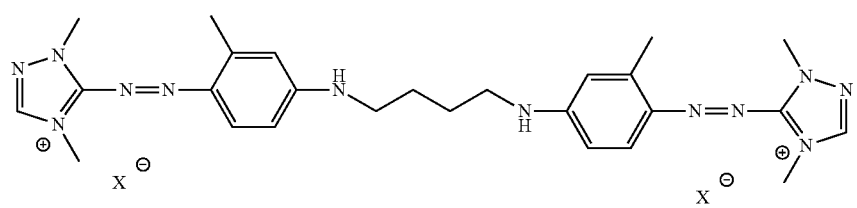

5-[2-(4-{[5-({4-[2-(1,4-dimethyl-1H-1,2,4-triazol-4-ium-5-yl)diazen-1-yl]-2-methylphenyl}amino)pentyl]amino}-3-methylphenyl)diazen-1-yl]-1,4-dimethyl-1H-1,2,4-triazol-4-ium salts

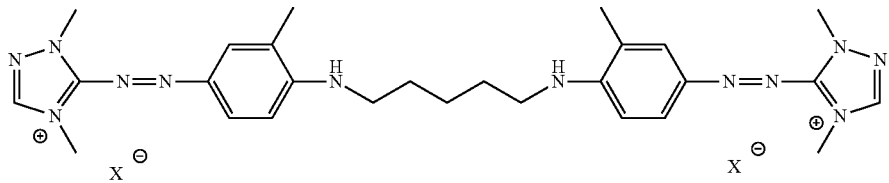

5-[2-(4-{[5-({4-[2-(1,4-dimethyl-1H-1,2,4-triazol-4-ium-5-yl)diazen-1-yl]-3-methylphenyl}amino)pentyl]amino}-2-methylphenyl)diazen-1-yl]-1,4-dimethyl-1H-1,2,4-triazol-4-ium salts

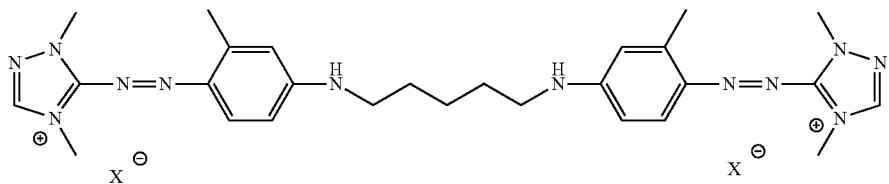

5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium salts

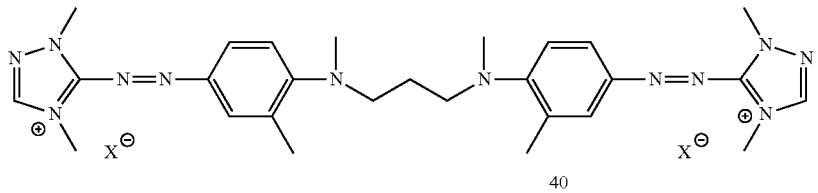

5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium salts

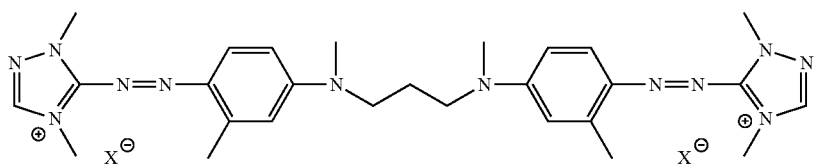

5-[2-(4-{[4-({4-[2-(1,4-dimethyl-1H-1,2,4-triazol-4-ium-5-yl)diazen-1-yl]-2-methylphenyl}(methyl)amino)butyl](methyl)amino}-3-methylphenyl)diazen-1-yl]-1,4-dimethyl-1H-1,2,4-triazol-4-ium salts

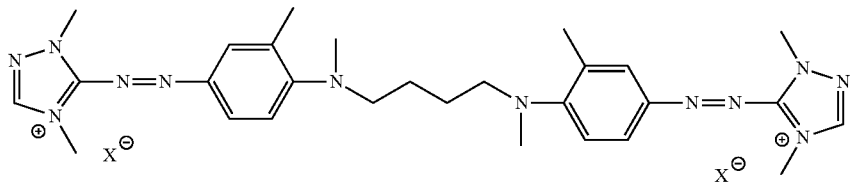

5-[2-(4-{[4-({4-[2-(1,4-dimethyl-1H-1,2,4-triazol-4-ium-5-yl)diazen-1-yl]-3-methylphenyl}(methyl)amino)butyl](methyl)amino}-2-methylphenyl)diazen-1-yl]-1,4-dimethyl-1H-1,2,4-triazol-4-ium salts

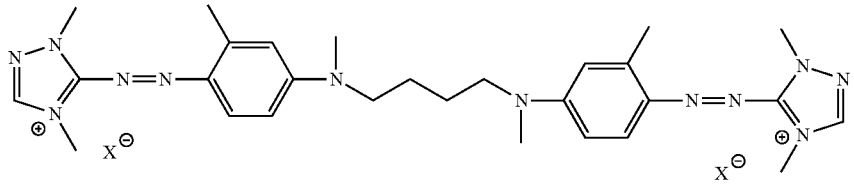

5-[2-(4-{[5-({4-[2-(1,4-dimethyl-1H-1,2,4-triazol-4-ium-5-yl)diazen-1-yl]-2-methylphenyl}(methyl)amino)pentyl](methyl)amino}-3-methylphenyl)diazen-1-yl]-1,4-dimethyl-1H-1,2,4-triazol-4-ium salts

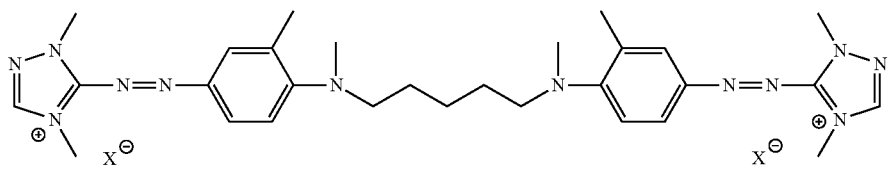

5-[2-(4-{[5-({4-[2-(1,4-dimethyl-1H-1,2,4-triazol-4-ium-5-yl)diazen-1-yl]-3-methylphenyl}(methyl)amino)pentyl](methyl)amino}-2-methylphenyl)diazen-1-yl]-1,4-dimethyl-1H-1,2,4-triazol-4-ium salts

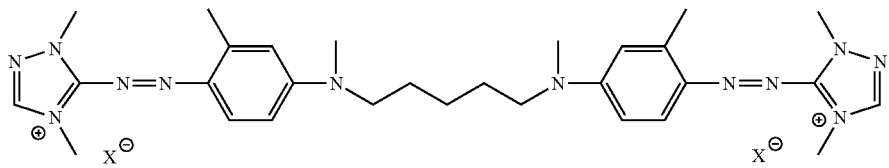

5-[2-(4-{[3-({4-[2-(1,4-dimethyl-1H-1,2,4-triazol-4-ium-5-yl)diazen-1-yl]-2-methoxyphenyl}amino)propyl]amino}-3-methoxyphenyl)diazen-1-yl]-1,4-dimethyl-1H-1,2,4-triazol-4-ium salts

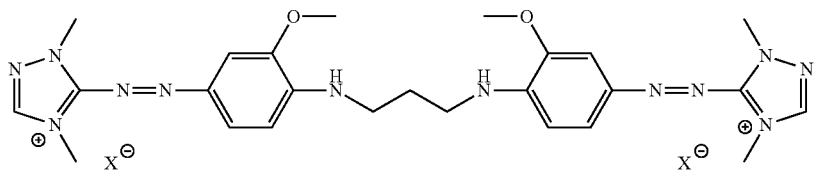

5-[2-(4-{[3-({4-[2-(1,4-dimethyl-1H-1,2,4-triazol-4-ium-5-yl)diazen-1-yl]-3-methoxyphenyl}amino)propyl]amino}-2-methoxyphenyl)diazen-1-yl]-1,4-dimethyl-1H-1,2,4-triazol-4-ium salts

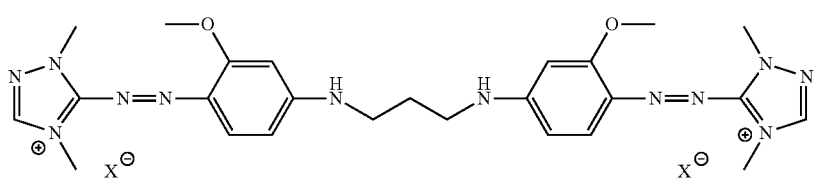

5-[2-(4-{[4-({4-[2-(1,4-dimethyl-1H-1,2,4-triazol-4-ium-5-yl)diazen-1-yl]-2-methoxyphenyl}amino)butyl]amino}-3-methoxyphenyl)diazen-1-yl]-1,4-dimethyl-1H-1,2,4-triazol-4-ium salts

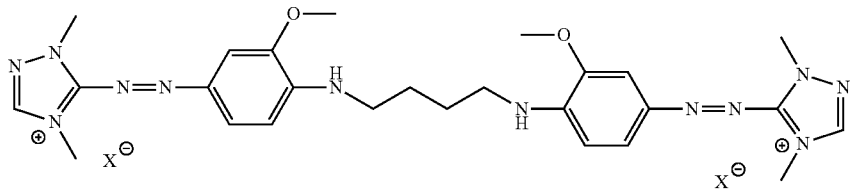

5-[2-(4-{[4-({4-[2-(1,4-dimethyl-1H-1,2,4-triazol-4-ium-5-yl)diazen-1-yl]-3-methoxyphenyl}amino)butyl]amino}-2-methoxyphenyl)diazen-1-yl]-1,4-dimethyl-1H-1,2,4-triazol-4-ium salts

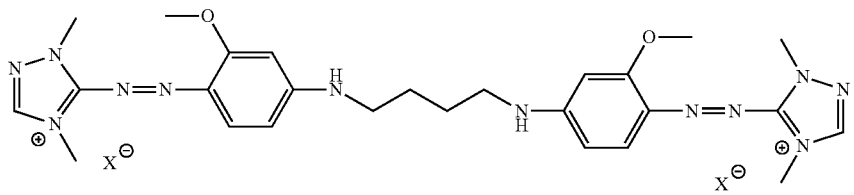

5-[2-(4-{[5-({4-[2-(1,4-dimethyl-1H-1,2,4-triazol-4-ium-5-yl)diazen-1-yl]-2-methoxyphenyl}amino)pentyl]amino}-3-methoxyphenyl)diazen-1-yl]-1,4-dimethyl-1H-1,2,4-triazol-4-ium salts

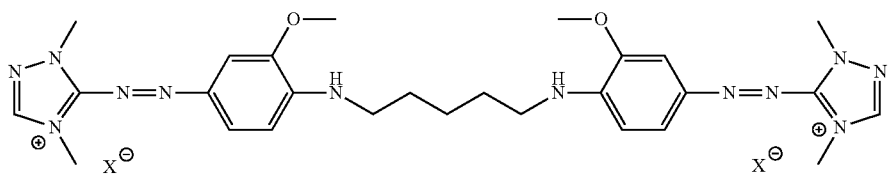

5-[2-(4-{[5-({4-[2-(1,4-dimethyl-1H-1,2,4-triazol-4-ium-5-yl)diazen-1-yl]-3-methoxyphenyl}amino)pentyl]amino}-2-methoxyphenyl)diazen-1-yl]-1,4-dimethyl-1H-1,2,4-triazol-4-ium salts

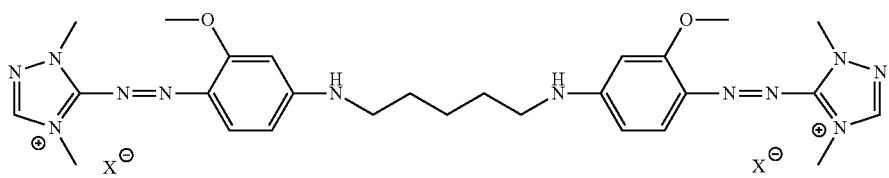

5-[2-(4-{[3-({4-[2-(1,4-dimethyl-1H-1,2,4-triazol-4-ium-5-yl)diazen-1-yl]-2-methoxyphenyl}(methyl)amino)propyl](methyl)amino}-3-methoxyphenyl)diazen-1-yl]-1,4-dimethyl-1H-1,2,4-triazol-4-ium salts

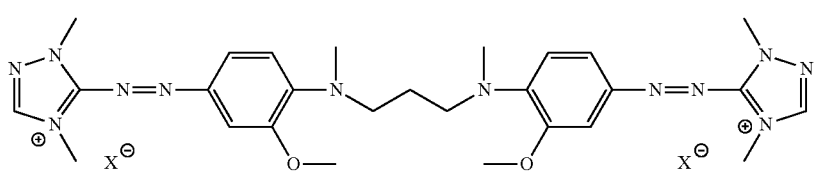

5-[2-(4-{[3-({4-[2-(1,4-dimethyl-1H-1,2,4-triazol-4-ium-5-yl)diazen-1-yl]-3-methoxyphenyl}(methyl)amino)propyl](methyl)amino}-2-methoxyphenyl)diazen-1-yl]-1,4-dimethyl-1H-1,2,4-triazol-4-ium salts

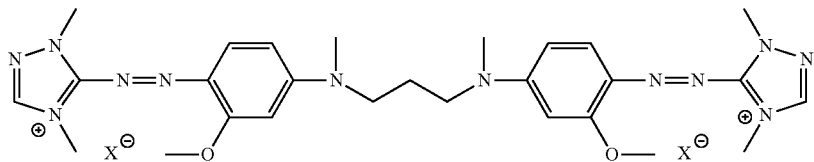

5-[2-(4-{[4-({4-[2-(1,4-dimethyl-1H-1,2,4-triazol-4-ium-5-yl)diazen-1-yl]-2-methoxyphenyl}(methyl)amino)butyl](methyl)amino}-3-methoxyphenyl)diazen-1-yl]-1,4-dimethyl-1H-1,2,4-triazol-4-ium salts

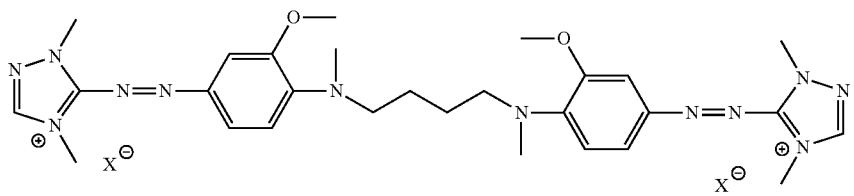

5-[2-(4-{[4-({4-[2-(1,4-dimethyl-1H-1,2,4-triazol-4-ium-5-yl)diazen-1-yl]-3-methoxyphenyl}(methyl)amino)butyl](methyl)amino}-2-methoxyphenyl)diazen-1-yl]-1,4-dimethyl-1H-1,2,4-triazol-4-ium salts

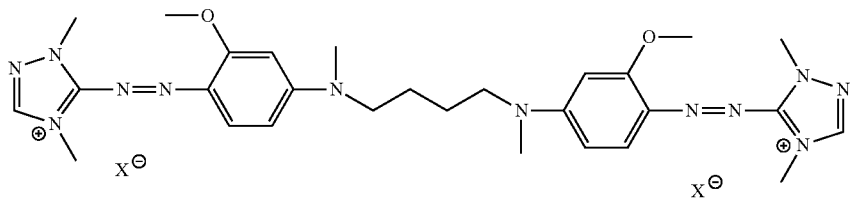

5-[2-(4-{[5-({4-[2-(1,4-dimethyl-1H-1,2,4-triazol-4-ium-5-yl)diazen-1-yl]-2-methoxyphenyl}(methyl)amino)pentyl](methyl)amino}-3-methoxyphenyl)diazen-1-yl]-1,4-dimethyl-1H-1,2,4-triazol-4-ium salts

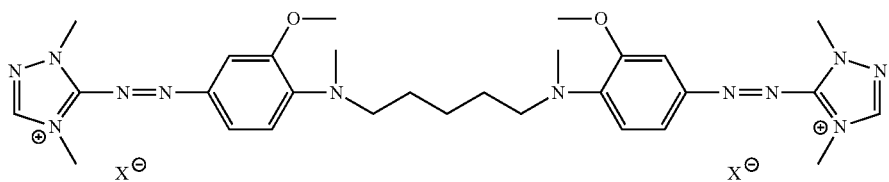

5-[2-(4-{[5-({4-[2-(1,4-dimethyl-1H-1,2,4-triazol-4-ium-5-yl)diazen-1-yl]-3-methoxyphenyl}(methyl)amino)pentyl](methyl)amino}-2-methoxyphenyl)diazen-1-yl]-1,4-dimethyl-1H-1,2,4-triazol-4-ium salts

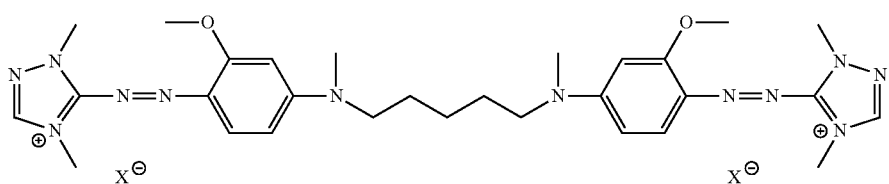

The compounds cited above are dicationic dimeric dyes, wherein the organic dication is neutralized by two anions X—. The anions X— are physiologically acceptable anions, preferably from the group formed by chloride, bromide, iodide, methyl sulphate, methyl sulphonate, p-toluenesulphonate, acetate, hydrogen sulphate, ½ sulphate or ½ tetrachlorozincate.

In the context of the studies which led to this disclosure, it was shown that with the direct dyes (a) with formula (I), particularly intensive and oxidation-stable colours could be obtained when:

Het1, Het2 independently of each other represent one of the structures (II), (III) or (IV)

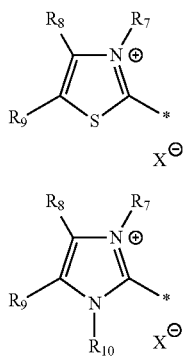

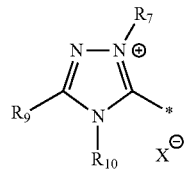

R1, R3 both represent a methyl group
R2, R4 both represent a hydrogen atom
R5, R6 independently of each other represent hydrogen or a $C_1$-$C_6$ alkyl group
R7, R10 both represent a methyl group
R8, R9 both represent a hydrogen atom
Q represents a group with formula (VIII):

$$* —(CH_2)_n-* \qquad (VIII)$$

and n represents the number 3 or 4.

Specifically more particularly preferred agents are therefore agents, in accordance with an exemplary embodiment of the present disclosure, for colouring keratinic fibers, which contain at least one dye (a) with formula (I), selected from the group formed by 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts

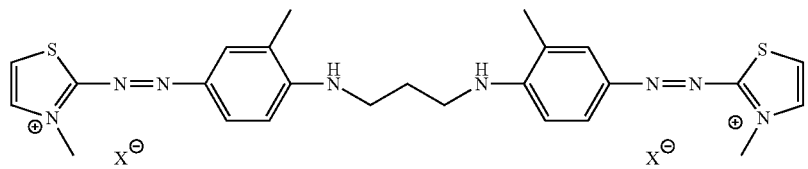

3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts

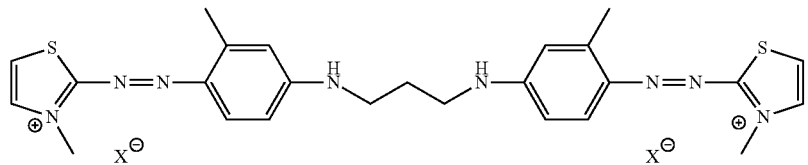

3-methyl-2-[2-(3-methyl-4-{[4-({2-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts

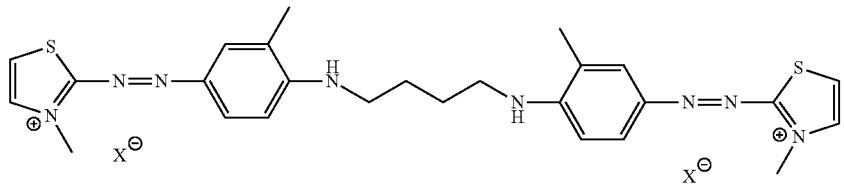

3-methyl-2-[2-(2-methyl-4-{[4-({3-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts

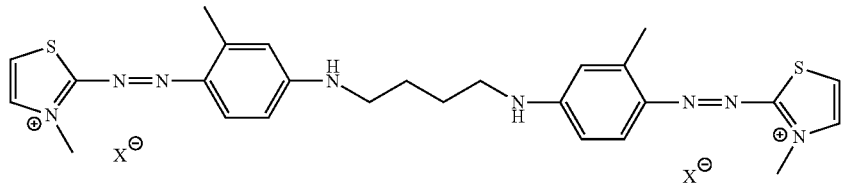

3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

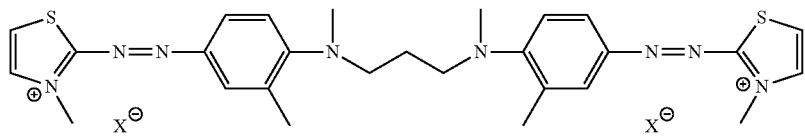

3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

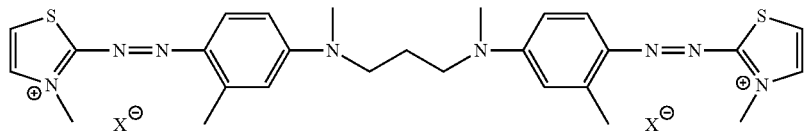

3-methyl-2-(2-{3-methyl-4-[methyl({4-[methyl({2-methyl-4-[2-(3-methyl-1,3-thiazol-3-ium-2-yl)diazen-1-yl]phenyl})amino]butyl})amino]phenyl}diazen-1-yl)-1,3-thiazol-3-ium salts

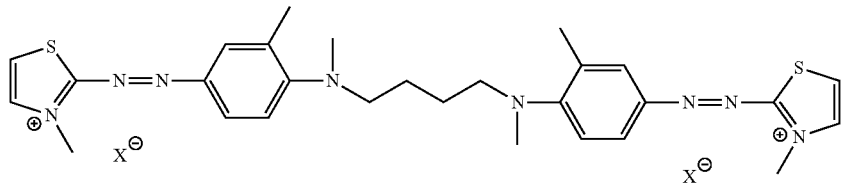

3-methyl-2-(2-{2-methyl-4-[methyl({4-[methyl({3-methyl-4-[2-(3-methyl-1,3-thiazol-3-ium-2-yl)diazen-1-yl]phenyl})amino]butyl})amino]phenyl}diazen-1-yl)-1,3-thiazol-3-ium salts

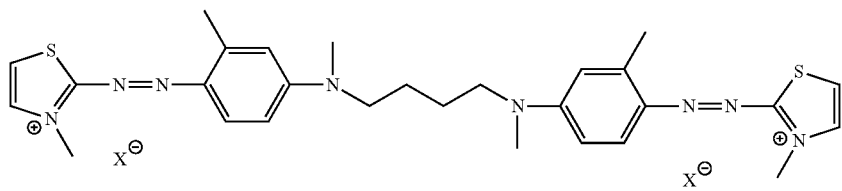

3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

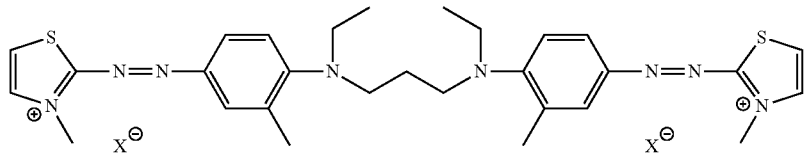

3-methyl-2-(2-{2-methyl-4-[ethyl({3-[ethyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium salts

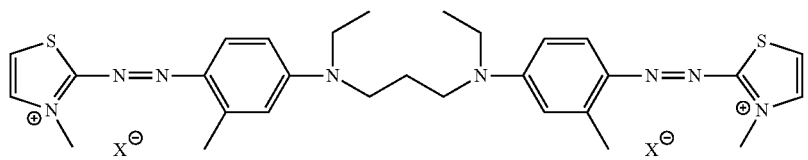

5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium salts

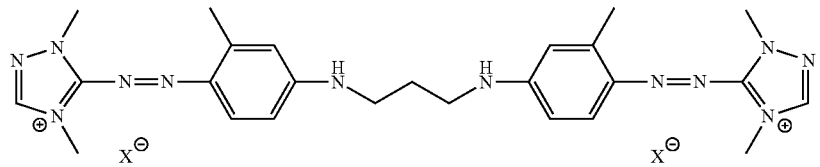

5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium salts

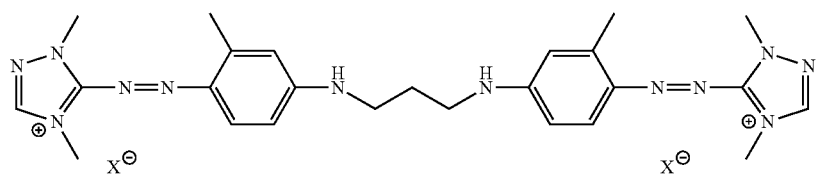

5-[2-(4-{[4-({4-[2-(1,4-dimethyl-1H-1,2,4-triazol-4-ium-5-yl)diazen-1-yl]-2-methylphenyl}amino)butyl]amino}-3-methylphenyl)diazen-1-yl]-1,4-dimethyl-1H-1,2,4-triazol-4-ium salts

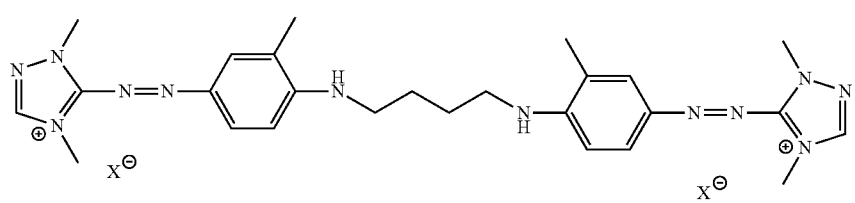

5-[2-(4-{[4-({4-[2-(1,4-dimethyl-1H-1,2,4-triazol-4-ium-5-yl)diazen-1-yl]-3-methylphenyl}amino)butyl]amino}-2-methylphenyl)diazen-1-yl]-1,4-dimethyl-1H-1,2,4-triazol-4-ium salts

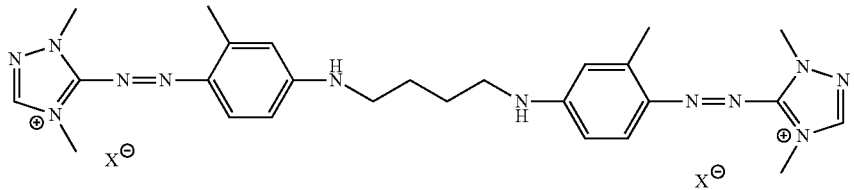

5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium salts

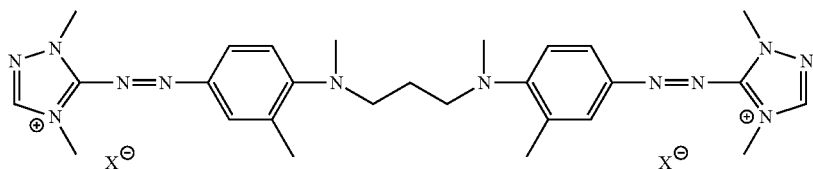

5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium salts

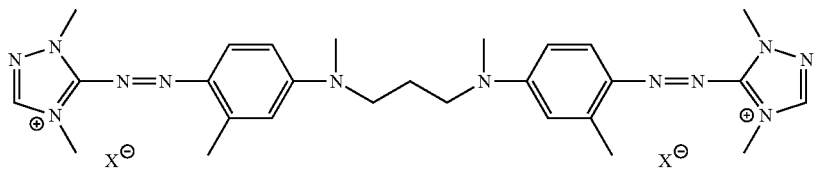

5-[2-(4-{[4-({4-[2-(1,4-dimethyl-1H-1,2,4-triazol-4-ium-5-yl)diazen-1-yl]-2-methylphenyl}(methyl)amino)butyl](methyl)amino}-3-methylphenyl)diazen-1-yl]-1,4-dimethyl-1H-1,2,4-triazol-4-ium salts

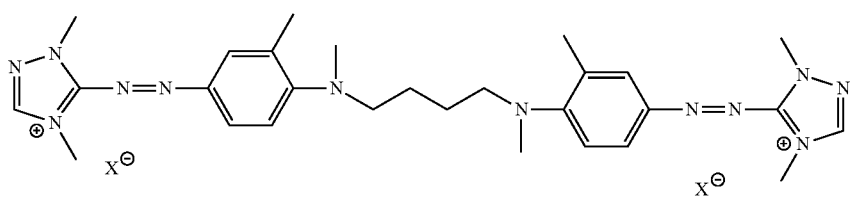

5-[2-(4-{[4-({4-[2-(1,4-dimethyl-1H-1,2,4-triazol-4-ium-5-yl)diazen-1-yl]-3-methylphenyl}(methyl)amino)butyl](methyl)amino}-2-methylphenyl)diazen-1-yl]-1,4-dimethyl-1H-1,2,4-triazol-4-ium salts

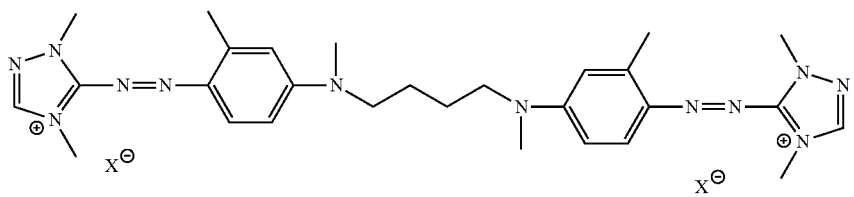

In a preferred embodiment, an agent in accordance with the present disclosure for colouring keratinic fibers is characterized in that it contains, as a dye with formula (a), at least one compound which is selected from the group formed by 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium dichloride 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium dibromide 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium sulphate 3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium di(toluenesulphonate)

3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium di(methylsulphate)

3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium tetrachlorozincate 3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium dichloride 3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium dibromide 3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium sulphate 3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium di(toluenesulphonate)

3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium di(methylsulphate)

3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium tetrachlorozincate 3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium dichloride 3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium dibromide 3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium sulphate 3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(toluenesulphonate)

3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(methylsulphate)

3-methyl-2-(2-{3-methyl-4-[methyl({3-[methyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium tetrachlorozincate 3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium dichloride 3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium dibromide 3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium sulphate 3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(toluenesulphonate)

3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(methylsulphate)

3-methyl-2-(2-{2-methyl-4-[methyl({3-[methyl({3-methyl-4-[2-(3-methyl-1,3-thiazol-3-ium-2-yl)diazen-1-yl]phenyl})amino]propyl})amino]phenyl}diazen-1-yl)-1,3-thiazol-3-ium tetrachlorozincate 5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium dichloride 5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium dibromide 5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium sulphate 5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium di(toluenesulphonate)

5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium di(methylsulphate)

5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium tetrachlorozincate 5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium dichloride 5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium dibromide 5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium sulphate 5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium di(toluenesulphonate)

5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium di(methylsulphate)

5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium tetrachlorozincate 5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium dichloride 5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium dibromide 5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium sulphate 5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium di(toluenesulphonate)

5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium di(methylsulphate)

5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium tetrachlorozincate 5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium dichloride 5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium dibromide 5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium sulphate 5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium di(toluenesulphonate)

5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium di(methylsulphate)

5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium tetrachlorozincate.

In an explicitly most particularly preferred embodiment, an agent in accordance with the present disclosure for colouring keratinic fibers is characterized in that it contains, as the dye with formula (a), at least one compound which is selected from the group formed by 3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium

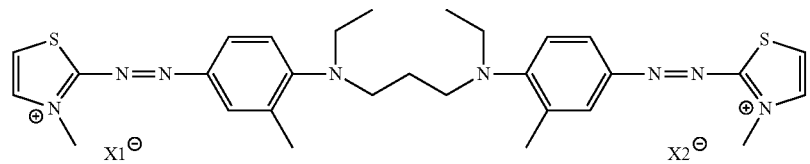

3-methyl-2-(2-{3-methyl-4-[ethyl({3-[ethyl(2-methyl-4-[2-(3-methyl-1,3-thiazol-3-ium-2-yl)diazen-1-yl]phenyl})amino]propyl})amino]phenyl}diazen-1-yl)-1,3-thiazol-3-ium dichloride 3-methyl-2-(2-{3-methyl-4-[ethyl({3-[ethyl(2-methyl-4-[2-(3-methyl-1,3-thiazol-3-ium-2-yl)diazen-1-yl]phenyl})amino]propyl})amino]phenyl}diazen-1-yl)-1,3-thiazol-3-ium dibromide 3-methyl-2-(2-{3-methyl-4-[ethyl({3-[ethyl(2-methyl-4-[2-(3-methyl-1,3-thiazol-3-ium-2-yl)diazen-1-yl]phenyl})amino]propyl})amino]phenyl}diazen-1-yl)-1,3-thiazol-3-ium sulphate 3-methyl-2-(2-{3-methyl-4-[ethyl({3-[ethyl(2-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(toluenesulphonate)

3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(methylsulphate)

3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium tetrachlorozincate

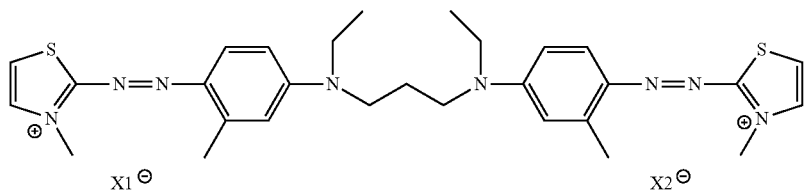

3-methyl-2-(2-{2-methyl-4-[ethyl({3-[ethyl(3-methyl-4-[2-(3-methyl-1,3-thiazol-3-ium-2-yl)diazen-1-yl]phenyl})amino]propyl})amino]phenyl}diazen-1-yl)-1,3-thiazol-3-ium dichloride 3-methyl-2-(2-{2-methyl-4-[ethyl({3-[ethyl(3-methyl-4-[2-(3-methyl-1,3-thiazol-3-ium-2-yl)diazen-1-yl]phenyl})amino]propyl})amino]phenyl}diazen-1-yl)-1,3-thiazol-3-ium dibromide 3-methyl-2-(2-{2-methyl-4-[ethyl({3-[ethyl(3-methyl-4-[2-(3-methyl-1,3-thiazol-3-ium-2-yl)diazen-1-yl]phenyl})amino]propyl})amino]phenyl}diazen-1-yl)-1,3-thiazol-3-ium sulphate 3-methyl-2-(2-{2-methyl-4-[ethyl({3-[ethyl(3-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(toluenesulphonate)

3-methyl-2-(2-{2-methyl-4-[ethyl({3-[ethyl(3-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(methylsulphate)

3-methyl-2-(2-{2-methyl-4 ethyl({3-[ethyl({3-methyl-4-[2-(3-methyl-1,3-thiazol-3-ium-2-yl]diazen-1-yl]phenyl})amino]propyl})amino]phenyl}diazen-1-yl)-1,3-thiazol-3-ium tetrachlorozincate.

The inventive agents for changing the colour of keratinic fibers preferably contain the direct dye or dyes with formula (I) in a total quantity of about 0.01% to about 4.5% by weight, preferably about 0.05% to about 2.8% by weight, more preferably about 0.1% to about 2.2% by weight and particularly preferably about 0.2% to about 1.2% by weight. The quantities given as the percentage by weight in this regard are with respect to the total quantity of all of the compounds with formula (I) contained in the agent, which are related to the total weight of the agent.

In a further preferred embodiment, an inventive agent for colouring keratinic fibers is herein characterized in that—with respect to the total weight of the agent—it contains one or more direct dyes (a) with formula (I) in a total quantity of about 0.01% to about 4.5% by weight, preferably about 0.05% to about 2.8% by weight, more preferably about 0.1% to about 2.2% by weight and particularly preferably about 0.2% to about 1.2% by weight.

The dyes with general formula (I) may, for example, be produced in accordance with a method as described in WO 2002/100369 A2.

Thus, for example, the 2-aminothiazole educt can be reacted in concentrated sulphuric acid with nitrosylsulphuric acid to form the diazonium ion:

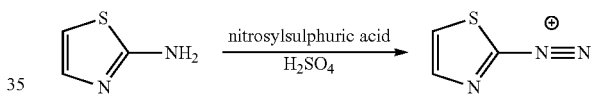

The reactive diazonium ion then undergoes a double azo coupling reaction with dimeric aniline derivatives:

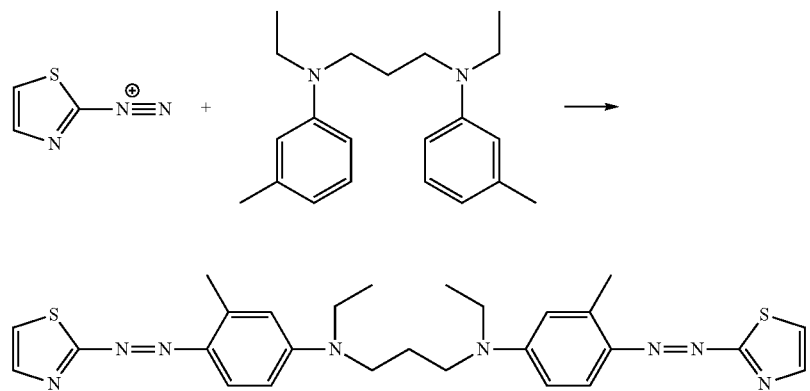

The educt N,N'-diethyl-N,N'-bis(3-methylphenyl)-1,3-propandiamine used in the azo coupling reaction and the analogous compounds thereof may, for example, be produced as described in U.S. Pat. No. 4,562,249.

The neutral dimeric dye resulting from the azo coupling reaction may then finally be quaternized with quaternization agents. The quaternizing reaction is preferably carried out in a polar aprotic solvent (such as DMSO, DMF, etc, for example). Examples of the quaternization agents are dimethyl sulphate, methyl bromide or p-toluenesulphonate.

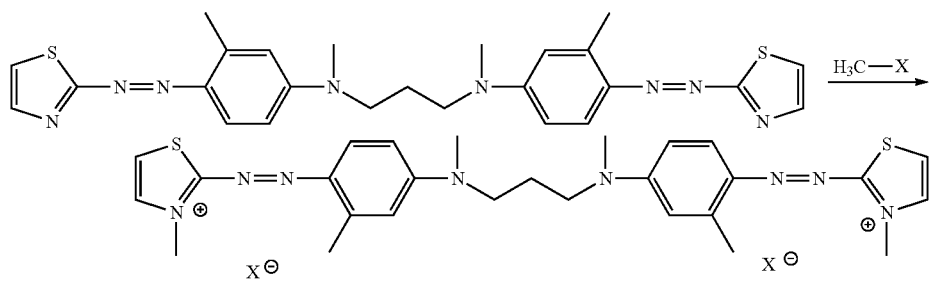

A central tenet of the present application is based on the preparation of colorants with direct dyes which have a high oxidation stability and thus can permit the simultaneous ultra-lightening and colour of keratinic fibers. Surprisingly, the direct dyes with formula (I) exhibited a particularly high stability as regards a mixture of hydrogen peroxide and persulphates. In order to permit simultaneous colouring and lightening, in a further preferred embodiment, the agents in accordance with the present disclosure additionally contain hydrogen peroxide.

In a further preferred embodiment, hydrogen peroxide itself is used as the aqueous solution. The concentration of a hydrogen peroxide solution in the agent in accordance with an exemplary embodiment of the present disclosure is on the one hand determined by legal requirements and on the other hand determined by the desired effect; preferably, about 6% to about 12% by weight solutions in water are used. Preferred inventive agents of the first inventive concept which are ready for use are characterized in that, with respect to the total weight of the ready-to-use agent, they contain about 0.5% to about 12.5% by weight, particularly preferably about 2.5% to about 10% by weight, and in particular about 4.0% to about 9.0% by weight of hydrogen peroxide, respectively with respect to the total weight of the agent.

In a further preferred embodiment, an agent in accordance with the present disclosure is characterized in that—with respect to the total weight of the agent—it contains about 0.5% to about 12.5% by weight, preferably about 2.5% to about 10% by weight and in particular about 4.0% to about 9.0% by weight of hydrogen peroxide.

In order to obtain an ultra-lightening and bleaching action, the agent may further contain a peroxo salt. Suitable peroxo salts are inorganic peroxo compounds, preferably selected from the group formed by ammonium peroxodisulphate, alkali metal peroxodisulphates, ammonium peroxomonosulphate, alkali metal peroxomonosulphates, alkali metal peroxodiphosphates and alkaline earth metal peroxides. Peroxodisulphates, in particular ammonium peroxodisulphate, potassium peroxodisulphate and sodium peroxodisulphate, are particularly preferred.

In a further particularly preferred embodiment, an agent in accordance with the present disclosure is characterized in that it contains at least one persulphate from the group ammonium peroxodisulphate, potassium peroxodisulphate and sodium peroxodisulphate.

The term "ammonium peroxodisulphate" means a compound with formula $(NH_4)_2S_2O_8$. The term "potassium peroxodisulphate" means a compound with formula $K_2S_2O_8$. The term "sodium peroxodisulphate" means a compound with formula $Na_2S_2O_8$.

The persulphates are respectively contained in the agent, in accordance with an exemplary embodiment of the present disclosure, in a quantity of about 0.5% to about 20% by weight, preferably about 1% to about 12.5% by weight, particularly preferably about 2.5% to about 10% by weight and in particular about 3% to about 6% by weight, with respect to the total weight of the ready-to-use agent.

In a further particularly preferred embodiment, an agent in accordance with the present disclosure is characterized in that—with respect to the total weight of the agent—it contains one or more persulphates from the group ammonium peroxodisulphate, potassium peroxodisulphate and sodium peroxodisulphate in a total quantity of about 0.5% to about 20% by weight, preferably about 1.0% to about 12.5% by weight, more preferably about 2.5% to about 10% by weight and particularly preferably about 3.0% to about 6.0% by weight.

The direct dyes in accordance with the present disclosure with general formula (I) have been shown to be particularly stable with respect to specific mixtures of ammonium peroxodisulphate, potassium peroxodisulphate and sodium peroxodisulphate.

In a further particularly preferred embodiment, an agent in accordance with the present disclosure is characterized in that—with respect to the total weight of the agent—it contains about 0.2% to about 13.5% by weight, preferably about 0.5% to about 1.5% by weight, of ammonium peroxodisulphate about 0.5% to about 4.5% by weight, preferably about 1.5% to about 2.5% by weight, of potassium peroxodisulphate, and about 0.2% to about 1.8% by weight, preferably about 0.4% to about 0.8% by weight, of sodium peroxodisulphate.

In order to strengthen the bleaching effect, the colour changing agent, in accordance with an exemplary embodiment of the present disclosure, may contain further bleaching power boosters such as, for example, tetraacetylethylendiamine (TAED), 1,5-diacetyl-2,4-dioxohexahydro-1,3,5-triazine (DADHT), tetraacetylglycoluril (TAGU), N-nonanoylsuccinimide (NOSI), n-nonanoyl or isononanoyl oxybenzenesulphonate (n- or i-NOBS), phthalic acid anhydride, triacetin, ethyleneglycol diacetate and 2,5-diacetoxy-2,5-dihydrofuran as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate and calcium carbonate, and nitrogen-containing, heterocyclic bleaching power boosters such as 4-acetyl-1-methylpyridinium-p-toluenesulphonate, 2-acetyl-1-methylpyridinium-p-toluenesulphonate, as well as N-methyl-3,4-dihydroi soquinolinium-p-toluenesulphonate.

To further enhance lightening, the composition in accordance with an exemplary embodiment of the present disclosure may additionally be supplemented with at least one $SiO_2$ compound such as silica or silicates, in particular water glasses. In accordance with an exemplary embodiment of the present disclosure, it may be of particular advantage to add the $SiO_2$ compounds in quantities of about 0.05% by weight to about 15% by weight, particularly preferably in quantities of about 0.15% by weight to about 10% by weight and more particularly preferably in quantities of about 0.2% by weight to about 5% by weight, respectively with respect to the anhydrous composition in accordance with the present disclosure. The quantities by weight in this regard respectively reflect the quantity of the $SiO_2$ compounds (without their water fraction) in the agents.

In a further preferred embodiment, in addition to the compound with formula (I), the agents in accordance with the present disclosure additionally contain at least one further direct dye. The combination with further cationic direct dyes means that the nuance spectrum can be broadened further, and the colouring properties are improved still further.

In a further more particularly preferred embodiment, an agent in accordance with the present disclosure is characterized in that it contains at least one $SiO_2$ compound from the group formed by silicas, silicates, water glasses and/or alkali metal metasilicates.

For even further nuancing, the agent in accordance with an exemplary embodiment of the present disclosure for changing the colour of keratinic fibers additionally also contains at least one further direct dye. Direct dyes can be divided into anionic, cationic and non-ionic direct dyes.

The direct dyes are preferably selected from the cationic direct dyes, because these are highly compatible with the dyes with general formula (I).

In a further particularly preferred embodiment, an agent in accordance with the present disclosure is characterized in that it additionally contains at least one further cationic direct dye which differs from the dyes with formula (I).

The term "cationic dyes" in this context should be understood to mean dyes which carry at least one positive charge.

One or more dyes from the following group have been shown to be particularly compatible: Basic Yellow 87, Basic Orange 31, Basic Red 51, Basic Violet 2 and Cationic Blue 347.

Dyes with formula (I) are particularly compatible with the cationic azo dyes Basic Orange 31 and Basic Red 51. By combining a dye with formula (I) with Basic Orange 31 and/or Basic Red 51, nuances over the entire colour spectrum can be obtained—apart from pure yellow nuances.

In a further particularly preferred embodiment, an agent in accordance with the present disclosure is characterized in that it additionally contains Basic Orange 31 and/or Basic Red 51.

The agent in accordance with the present disclosure may, however, also additionally contain at least one nonionic direct dye. This may be selected from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxy-ethyl)aminophenol, 2-(2-hydroxyethyl) amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl) amino]-3-nitrophenol, 4-nitro-o-phenylendiamine, 6-nitro-1,2,3,4-tetrahydroquinoxaline, 2-hydroxy-1,4-naphthoquinone, picramic acid and its salts, 2-amino-6-chloro-4-nitrophenol, 4-ethyl-amino-3-nitrobenzoic acid and 2-chloro-6-ethylamino-4-nitrophenol.

In addition, anionic direct dyes may also be included which are known by the international descriptions or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. The agents in accordance with an exemplary embodiment of the present disclosure may also be used together with oxidation dyes. Such oxidation dyes additionally contain at least one oxidation dye precursor, preferably at least one oxidation dye precursor of the developer type and at least one oxidation dye precursor of the coupler type. Particularly suitable oxidation dye precursors of the developer type are selected from at least one compound from the group formed by p-phenylendiamine, p-toluylenediamine, 2-(2-hydroxyethyl)-p-phenylendiamine, 2-(1,2-dihydroxyethyl)-p-phenylendiamine, N,N-bis-(2-hydroxyethyl)-p-phenylendiamine, 2-methoxymethyl-p-phenylendiamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)-methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)-phenol, 4,5-diamino-1-(2-hydroxyethyl) pyrazole, 2,4,5,6-tetraaminopyrimidine, 4-hydroxy-2, 5,6-triaminopyrimidine, 2-hydroxy-4,5,6-triaminopyrimidine, 2,3-diamino-6,7-dihydro-1H,5H-pyrazolo[1,2-a]pyrazol-1-one as well as their physiologically acceptable salts.

Particularly suitable oxidation dye precursor of the coupler type are selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylendiamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholino-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds, or their physiologically acceptable salts.

The additional direct dyes, developer components and coupling components are preferably used in a fraction of about 0.0001% to about 5.0% by weight, preferably about 0.001% to about 3.5% by weight, respectively with respect to the ready-to-use agent. In this regard, developer components and coupler components are generally used in approximately molar quantities with respect to each other. Although molar use has proved to be appropriate, a small surplus of individual oxidation dye precursors is not disadvantageous, so that developer components and coupling components may be present in a molar ratio of about 1 to 0.5 to about 1 to 3, in particular about 1 to 1 up to about 1 to 2.

The dyes may also contain additional substances, excipients and additives in order to improve the colouring power and to provide the agent with other desirable properties.

Preferably, the ready-to-use dyes are prepared as a liquid preparation and for this purpose, a surfactant substance is additionally added to the agents, wherein such surfactant substances, depending on the field of application, are described as surfactants or as emulsifying agents; they are preferably selected from anionic, cationic, zwitterionic, amphoteric and nonionic surfactants and emulsifying agents.

Agents in accordance with an exemplary embodiment of the present disclosure which are preferred are thus characterized in that the agent additionally contains an anionic surfactant. Preferred anionic surfactants are fatty acids, alkyl sulphates, alkylether sulphates and ether carbonic acids containing 10 to 20 C atoms in the alkyl group and up to 16 glycolether groups in the molecule. The anionic surfactants are employed in proportions of about 0.1% to about 45% by weight, preferably about 1% to about 30% by weight, and more particularly preferably about 1% to about 15% by weight, with respect to the total quantity of the ready-to-use agent.

Preferred agents in accordance with an exemplary embodiment of the present disclosure are characterized in that the agent additionally contains at least one zwitterionic surfactant. Preferred zwitterionic surfactants are betains, N-alkyl-N,N-dimethylammonium glycinates, N-acyl-aminopropyl-N,N-dimethylammonium glycinates and 2-alkyl-3-carboxymethyl-3-hydroxyethyl imidazoline. A preferred zwitterionic surfactant is known by the INCI designation of Cocamidopropyl Betaine.

Preferred agents in accordance with an exemplary embodiment of the present disclosure are characterized in that the agent additionally contains at least one amphoteric surfactant. Preferred amphoteric surfactants are N-alkylgly-cines, N-alkylpropionic acids, N-alkylaminobutyric acids, N-alkyliminodipropionic acids, N-hydroxyethyl-N-alkyl-amidopropylglycines, N-alkyltaurines, N-alkylsarcosine, 2-alkylaminopropionic acids and alkylaminoacetic acids. Particularly preferred amphoteric surfactants are N-coco-alkylaminopropionate, coco-acylaminoethylaminopropionate and $C_{12}$-$C_{18}$-acylsarcosine.

Furthermore, it has been shown to be advantageous for the agents to contain further non-ionogenic surface-active substances. Preferred nonionic surfactants are alkylpolyglyco-sides as well as alkylene oxide addition products with fatty alcohols and fatty acids each containing about 2 to about 30 mol of ethylene oxide per mol of fatty alcohol or fatty acid. Preparations with excellent properties are also obtained when they contain fatty acid esters of ethoxylated glycerine as the nonionic surfactants.

The nonionic, zwitterionic or amphoteric surfactants are employed in proportions of about 0.1% to about 45% by weight, preferably about 1% to about 30% by weight and more particularly preferably about 1% to about 15% by weight with respect to the total quantity of the ready-to-use agent.

Suitable agents in accordance with an exemplary embodiment of the present disclosure may also contain cationic surfactants of the quaternary ammonium compound, ester-quat and amidoamine type. Preferred quaternary ammonium compounds are ammonium halides as well as imidazolium compounds which are known by the INCI descriptions Quaternium-27 and Quatemium-83. Further cationic surfactants which may be used in accordance with an exemplary embodiment of the present disclosure are constituted by quaternized protein hydrolysates. A particularly suitable compound in accordance with an exemplary embodiment of the present disclosure from the amidoamine group is constituted by the commercially available stearamidopropyl-dimethylamine with the trade name Tegoamid® S 18. Preferred esterquats are quatemized ester salts of fatty acids with triethanolamine, quatemized ester salts of fatty acids with diethanolalkylamines and quaternized ester salts of fatty acids with 1,2-dihydroxypropyldialkylamines. The cationic surfactants are present in the agents used in accordance with an exemplary embodiment in proportions of about 0.05% to about 10% by weight with respect to the whole agent.

The ready-to-use dyes may also contain other auxiliary substances and additives. It has been shown to be advantageous if the agent contains at least one thickening agent. In principle, there are no restrictions regarding the nature of this thickening agent. Both organic and purely inorganic thickening agents may be used.

Suitable thickening agents are:
anionic synthetic polymers;
cationic synthetic polymers;
natural thickening agents such as nonionic guar gums, scleroglucan gums or xanthan gums, gum Arabic, gum ghatti, gum karaya, gum tragacanth, gum carrageenan, agar gum, carbo bean gum, pectins, alginates, starch fractions and derivatives such as amylose, amylopectin and dextrin, as well as cellulose derivatives such as, for example, methyl cellulose, carboxyalkyl celluloses and hydroxyalkyl celluloses;
nonionic fully synthetic polymers such as polyvinylalcohol or polyvinylpyrrolidinone; as well as
inorganic thickening agents, in particular phyllosilicates such as bentonite, for example, in particular smectites such as montmorillonite or hectorite.

Dyeing processes on keratinic fibers are usually carried out in an alkaline medium. In order to be as gentle as possible on the keratinic fibers and also on the skin, setting the pH too high is not desirable, however. Thus, preferably, the pH of the ready-to-use agent is between about 7 and about 11, in particular between about 8 and about 10.5. The term "pH" as used in the context of the present disclosure means pHs which are measured at a temperature of about 22° C.

The alkalization agents for setting the preferred pH in accordance with an exemplary embodiment may be selected from the group formed by ammonia, alkanolamines, basic amino acids, as well as inorganic alkalization agents such as alkali (alkaline-earth) metal hydroxides, alkali (alkaline-earth) metasilicates, alkali (alkaline-earth) phosphates and alkali (alkaline-earth) hydrogenophosphates. Preferred inorganic alkalization agent are magnesium carbonate, sodium hydroxide, potassium hydroxide, sodium silicate and sodium metasilicate. Organic alkalization agents which may be used in accordance with an exemplary embodiment are preferably selected from monoethanolamine, 2-amino-2-methylpropanol and triethanolamine. The basic amino acids which may be used in accordance with an exemplary embodiment as alkalization agents are preferably selected from the group formed by arginine, lysine, ornithine and histidine, particularly preferably arginine. However, in the context of the experiments carried out in respect of the present disclosure, it has been shown that further preferred agents in accordance with an exemplary embodiment are characterized in that they additionally contain an organic alkalization agent. One embodiment of the first inventive concept is characterized in that the agent additionally contains at least one alkalization agent which is selected from the group formed by ammonia, alkanolamines and basic amino acids, in particular from ammonia, monoethanolamine and arginine or its acceptable salts.

It has also been shown to be advantageous if the dyes, in particular when they additionally contain hydrogen peroxide, contain at least one stabilizer or complex-forming agent. Particularly preferred stabilizers are phenacetin, alkali benzoate (sodium benzoate) and salicylic acid. Furthermore, any complex-forming agent from the prior art may be used. Preferred complex-forming agents for use in accordance with an exemplary embodiment are nitrogen-containing polycarbonic acids, in particular EDTA and EDDS, and phosphonates, in particular 1-hydroxyethane-1,1-diphosphonate (HEDP) and/or ethylendiamine-tetramethylene phosphonate (EDTMP) and/or diethylenetriamine pentamethylene phosphonate (DTPMP) or their sodium salts.

Furthermore, the agents in accordance with an exemplary embodiment may contain further substances, excipients and additives such as, for example, nonionic polymers such as, for example, vinylpyrrolidinone/vinylacrylate copolymers, polyvinylpyrrolidinone, vinylpyrrolidinone/vinylacetate copolymers, polyethyleneglycols and polysiloxanes; additional silicones such as volatile or non-volatile, linear, branched or cyclic, cross-linked or non-cross-linked polyalkylsiloxanes (such as dimethicone or cyclomethicone), polyarylsiloxanes and/or polyalkylarylsiloxanes, in particular polysiloxanes with organofunctional groups such as substituted or unsubstituted amines (amodimethicone), carboxyl, alkoxy and/or hydroxyl groups (dimethicone copolyols), linear polysiloxane(A)-polyoxyalkylene(B) block copolymers, graft silicone polymers; cationic polymers such as quaternized cellulose ethers, polysiloxanes with quaternary groups, dimethyldiallylammonium chloride polymers, acrylamide-dimethyldiallyl-ammonium chloride copolymers, with diethyl sulphate-quaternized dimethylamino-ethylmethacrylate-vinyl pyrrolidinone copolymers, vinylpyrrolidinone-imidazolinium-methochloride copolymers and quaternized polyvinylalcohol; zwitterionic and amphoteric polymers; anionic polymers such as, for example, polyamino acids or cross-linked polyamino acids; structuring agents such as glucose, maleic acid and lactic acid, hair conditioning compounds such as phospholipids, for example lecithin and cephalin; fragrance oils, dimethylisosorbide and cyclodextrins; fibrous structure-improving substances, in particular mono-, di- and oligosaccharides such as, for example, glucose, galactose, fructose, fruit sugars and lactose; colorants to colour the agent; anti-dandruff substances such as piroctone olamine, zinc omadine and climbazole; amino acids and oligopeptides; animal and/or plant-based protein hydrolysates, as well as in the form of their fatty acid condensation products or, if appropriate, anionic or cationically modified derivatives; vegetable oils; light screening agents and UV blockers; substances such as panthenol, pantothenic acid, pantolactone, allantoin, pyrrolidinone carbonic acids and their salts, as well as bisabolol; polyphenols, in particular hydroxycinnamic acids, 6,7-dihydroxycoumarin, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; plumping and penetrating substances such as; glycerine, propyleneglycol monoethylether, carbonates, hydrogen carbonates, guanidine, ureas as well as primary, secondary and tertiary phosphates; opacifiers such as latex, styrene/PVP- and styrene/acryneglamide copolymers; pearlescent agents such as ethyleneglycol monostearate and distearate, as well as PEG-3-distearate; Pigments as well as propellants such as propane-butane-mixtures, $N_2O$, dimethylether, $CO_2$ and air.

The person skilled in the art will be able to select these further substances in accordance with the desired properties of the agent. As regards the further optional components as well as the quantities of these components used, reference should be made by the person skilled in the art to known relevant manuals. The additional substances and excipients are preferably used in quantities in the agents in accordance with an exemplary embodiment of respectively about 0.0001% to about 25% by weight, in particular about 0.0005% to about 15% by weight with respect to the total weight of the ready-to-use mixture.

The agents of the first aspect of the disclosure may be used in methods for colouring and also in methods for simultaneously bleaching or lightening and colouring human hair.

The agents in accordance with an exemplary embodiment of the present disclosure may be formulated as single component agents or as multi-component agents such as two-component agents or three-component agents and used appropriately. Separation into multi-component systems is particularly appropriate when the constituents are expected to be or risk being incompatible; the agent to be used in such systems is produced by the consumer directly before use by mixing the components.

The term "agent in accordance with the present disclosure for changing the colour of keratinic fibers" should always be understood to mean the ready-to-use agent.

If the agent in accordance with an exemplary embodiment of the present disclosure is made available to the user in the form of a single-component agent, then it is not necessary to have to produce the ready-to-use agent first, but it can be removed directly from the container in which it has been packaged and applied to the keratinic fibers.

Bleaching agents, however, are usually provided as two-component products in which an oxidizing agent-containing (A1) is mixed shortly before application with an (alkalization) agent (A2), and this ready-to-use mixture is applied to the hair.

In this case, the agent in accordance with an exemplary embodiment of the present disclosure is a ready-to-use agent which is produced by mixing (A1) and (A2) shortly before application.

In this regard, the direct dyes with general formula (I) can be formulated with the component (A1) (i.e. together with the oxidizing agent) or with component (A2) (together with the alkalization means).

It is also possible and within the scope of the disclosure for the ready-to-use agent to be produced shortly before application to human hair by mixing 3 components, wherein
  the component (A1) contains at least one direct dye with general formula (I) and at least one alkalization agent
  the component (A2) contains at least one first oxidizing agent (for example hydrogen peroxide), and
  the component (A3) contains at least one second oxidizing agent (for example one or more peroxodisulphate salts).

During the treatment time for the agent on the fibre, it may be advantageous to promote the lightening procedure or the cool-toning procedure by adding heat. The heat may be added via an external heat source, for example warm air from a warm air blower, and also, in particular when lightening the hair of living test persons, by means of the body temperature of the test person. In the latter case, usually, the person being treated is covered with a hood. A treatment phase at room temperature is also within the scope of the disclosure. In particular, the temperature during the treatment time is between about 20° C. and about 40° C., in particular between about 25° C. and about 38° C. After the end of the treatment time, the remaining colouring preparation is rinsed out of the hair with water or another cleaning agent. The cleaning agent here many in particular be commercially available shampoo, but in particular, the cleaning agent can be dispensed with and the rinsing procedure can be carried out with water when the lightening agent contains a support containing a lot of surfactant.

Further preferred embodiments of the use and method in accordance with the present disclosure follow mutatis mutandis from the agents in accordance with various exemplary embodiments described herein.

EXAMPLES

Direct dye 1: 3-methyl-2-(2-{3-methyl-4-[ethyl({3-[ethyl({2-methyl-4-[2-(3-methyl-1,3-thiazol-3-ium-2-yl)diazen-1-yl]phenyl})amino]propyl})amino]phenyl}diazen-1-yl)-1,3-thiazol-3-ium di(methylsulphate)

The dye DZ 1 was synthesized using the method described in the documents WO 2002/100369 A2 and U.S. Pat. No. 4,562,249.

DZ 1 (in accordance with an exemplary embodiment of the present disclosure)

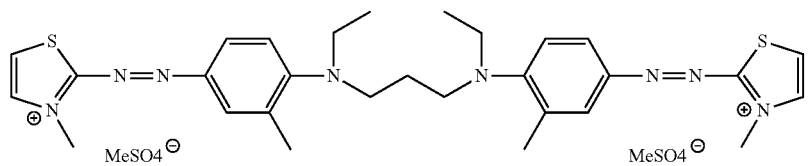 [SMILES: "MeSO4" ; "MeSO4" ; CCN(CCCN(CC)c1ccc(N=Nc2scc[n+]2C)cc1C)c1ccc(N=Nc2scc[n+]2C)cc1C]

Direct dye 2: 3-methyl-2-(2-{4-[methyl({3-[methyl({4-[2-(3-methyl-1,3-thiazol-3-ium-2-yl)diazen-1-yl]phenyl})amino]propyl})amino]phenyl}diazen-1-yl)-1,3-thiazol-3-ium, di(methylsulphate)

(DZ 1, in accordance with an exemplary embodiment of the present disclosure)

The dye DZ 2 was synthesized using the method described in the documents WO 2002/100369 A2 and U.S. Pat. No. 3,291,788.

2-aminothiazole and N,N'-dimethyl-N,N'-diphenyl-propan-1,3-diamine were used as the educts (azo coupling reaction in aqueous solution acidified with sulphuric acid with nitrosylsulphuric acid). The neutral dye which was produced in this azo coupling reaction was then quaternized (for example with the quaternization agent dimethylsulphate in a polar aprotic solvent such as dimethylformamide or dimethylsulphoxide).

DZ 2 (Comparison)

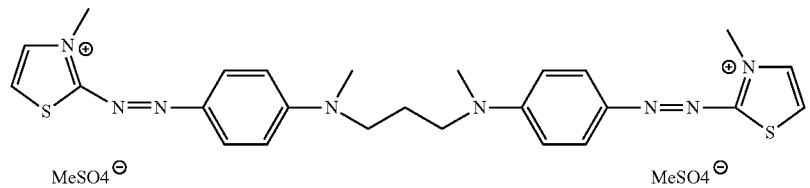 [SMILES: "MeSO4" ; "MeSO4" ; CN(CCCN(C)c1ccc(N=Nc2scc[n+]2C)cc1)c1ccc(N=Nc2scc[n+]2C)cc1]

Direct dye 3: 5-[2-(4-{[3-({4-[2-(1,4-dimethyl-1H-1,2,4-triazol-4-ium-5-yl)diazen-1-yl]phenyl}(methyl)amino)propyl](methyl)amino}phenyl)diazen-1-yl]-1,4-dimethyl-1H-1,2,4-triazol-4-ium di(methylsulphate)

The dye DZ 3 was synthesized using a method as described in the document WO 2002/100369 A2.

DZ 3 (Comparison)

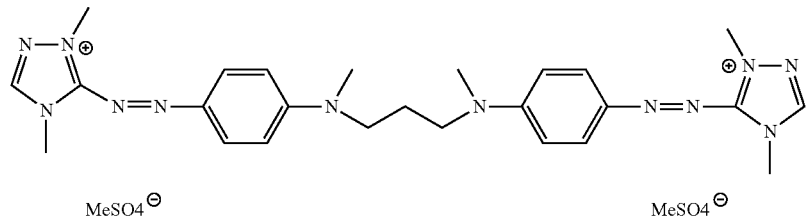 [SMILES: "MeSO4" ; "MeSO4" ; CN(CCCN(C)c1ccc(N=Nc2n(C)cn[n+]2C)cc1)c1ccc(N=Nc2n(C)cn[n+]2C)cc1]

Colour Examples
Formulations

The following colouring creams were produced (all given as the weight % of active substance)

| Colouring cream | E | V1 | V2 |
|---|---|---|---|
| Cetearyl alcohol | 3.5 | 3.5 | 3.5 |
| C12-C18 fatty alcohols | 0.9 | 0.9 | 0.9 |
| Ceteareth-20 | 0.1 | 0.1 | 0.1 |
| Quaternium-87 | 1.0 | 1.0 | 1.0 |
| Sodium laureth sulphate | 1.9 | 1.9 | 1.9 |
| Ammonium sulphate | 0.2 | 0.2 | 0.23 |
| Etidronic acid | 0.1 | 0.1 | 0.1 |
| Ammonium hydroxide | 0.1 | 0.1 | 0.1 |
| Sodium silicate | 0.2 | 0.2 | 0.2 |
| Ammonia (25% aqueous solution) | 2.5 | 2.5 | 2.5 |
| DZ1 (in accordance with an exemplary embodiment of the present disclosure) | 0.7 | — | — |
| DZ2 (comparison) | — | 0.7 | — |
| DZ3 (comparison) | — | — | 0.7 |
| Water | qsp 100 | qsp 100 | qsp 100 |

The direct dyes DZ1, DZ2 and DZ3 were each predissolved in a little water and mixed with the remaining formulation components.

The following developer emulsions were produced (total quantity 36 g)

| Developer emulsion | |
|---|---|
| Sodium hydroxide | 0.2 |
| Etidronic acid | 0.5 |
| Sodium laureth sulphate | 0.7 |
| Acrylate copolymer | 4.3 |
| Hydrogen peroxide (50% solution) | 8.0 |
| Water | 22.0 g |

The following bleaching powder was produced (total quantity 13.6 g).

| Developer emulsion | |
|---|---|
| Ammonium persulphate | 1.8 |
| Potassium persulphate | 5.8 |
| Sodium persulphate | 2.1 |
| Sodium silicate | 3.8 |
| Disodium EDTA | 0.1 |

Colorations 1.8 g of each colouring cream was applied to an approximately 6 cm long strand of human hair (Kerling Euro-natur hair, 80% grey) and left on for 30 minutes at 30° C. After the end of the treatment time, the hair was rinsed out, washed with a normal shampoo and then dried. After drying, the colour and the colour intensity of the strands were assessed visually under a daylight lamp.

| | Formulation | pH | Colour nuance | Colour intensity |
|---|---|---|---|---|
| E1 | DZ1 (in accordance with an exemplary embodiment of the present disclosure) | 9.5 | deep violet | ++++ |
| V1 | DZ2 (comparison) | 9.5 | pale violet | + |
| V2 | DZ3 (comparison) | 9.5 | pale pink | ++ |

Colour intensity: + = poor +++ = medium +++++ = very good

While at least one exemplary embodiment has been presented in the foregoing detailed description of the disclosure, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing an exemplary embodiment of the disclosure. It being understood that various changes may be made in the function and arrangement of elements described in an exemplary embodiment without departing from the scope of the disclosure as set forth in the appended claims.

The invention claimed is:

1. An agent for changing the colour of keratinic fibers, the agent comprising, in a cosmetic support, (a) at least one direct dye with formula (I), $$\text{Het1}-N=N-\underset{R_2}{\overset{R_1}{\bigcirc}}-\underset{R_5}{N}-Q-\underset{R_6}{N}-\underset{R_4}{\overset{R_3}{\bigcirc}}-N=N-\text{Het2} \quad (I)$$

wherein
one of Het1 and Het2 represents one of the structures (II), (III), (IV), (V), (VI) or (VII), and
the other of Het1 and Het2 represents one of the structures (III), (V), (VI) or (VII), (II) thiazolium ring with $R_7$, $R_8$, $R_9$ substituents, $X^\ominus$ counterion (III) imidazolium ring with $R_7$, $R_8$, $R_9$, $R_{10}$ substituents, $X^\ominus$ counterion (IV) triazolium ring with $R_7$, $R_9$, $R_{10}$ substituents, $X^\ominus$ counterion (V) thiadiazolium ring with $R_7$, $R_9$ substituents, $X^\ominus$ counterion

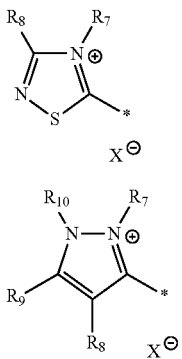

(VI)

(VII)

R1, R3 independently of each other represent a $C_1$-$C_6$ alkyl group or a $C_1$-$C_6$ alkoxy group,
R2, R4 each represent a hydrogen atom,
R5, R6 independently of each other represent a hydrogen atom, a $C_1$-$C_6$ alkyl group or a $C_2$-$C_6$ alkenyl group,
Q represents a group with formula (VIII), $$* —(CH_2)n-* \quad (VIII)$$

n represents a whole number from 3 to 6,
R7, R10 each independently of each other represent a $C_1$-$C_6$ alkyl group or a $C_2$-$C_6$ alkenyl group,
R8, R9 each independently of each other represent a hydrogen atom, a $C_1$-$C_6$ alkyl group, a halogen atom from the group chlorine, bromine, fluorine or iodine, a $C_1$-$C_6$ alkoxy group or a nitro group, and
X represents a physiologically acceptable anion selected from the group consisting of chloride, bromide, iodide, methyl sulphate, methyl sulphonate, p-toluenesulphonate, acetate, hydrogen sulphate, ½ sulphate or ½ tetrachlorozincate.

2. The agent as claimed in claim 1, wherein the agent comprises (a) at least one direct dye with general formula (I), in which
Het1, Het2 independently of each other respectively represent one of the structures (II), (III) or (IV):

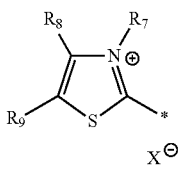

(II)

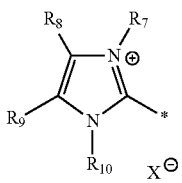

(III)

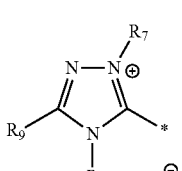

(IV)

3. The agent as claimed in claim 1, wherein the agent comprises (a) at least one direct dye with general formula (I), in which
R5, R6 independently of each other represent hydrogen or a $C_1$-$C_6$ alkyl group.

4. The agent as claimed in claim 1, wherein the agent comprises (a) at least one direct dye with general formula (I), in which
R7, R10 each independently of each other represent a methyl group or an ethyl group,
R8, R9 represents a hydrogen atom.

5. The agent as claimed in claim 1, wherein the agent comprises at least one direct dye with general formula (I) which is selected from:
3-methyl-2-[2-(3-methyl-4-{[3-({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts,
3-methyl-2-[2-(2-methyl-4-{[3-({3-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts,
3-methyl-2-[2-(3-methyl-4-{[4-({2-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts,
3-methyl-2-[2-(2-methyl-4-{[4-({3-methyl-4-[2-(3-methyl-1,3-thiazol-3-ium-2-yl)diazen-1-yl]phenyl}amino)butyl]amino}phenyl)diazen-1-yl]-1,3-thiazol-3-ium salts,
3-methyl-2-[2-(3-methyl-4-{[5-({2-methyl-4-[2-(3-methyl-1,3-thiazol-3-ium-2-yl)diazen-1-yl]phenyl}amino)pentyl]amino}phenyl)diazen-1-yl]-1,3-thiazol-3-ium salts,
3-methyl-2-[2-(2-methyl-4-{[5-({3-methyl-4-[2-(3-methyl-1,3-thiazol-3-ium-2-yl)diazen-1-yl]phenyl}amino)pentyl]amino}phenyl)diazen-1-yl]-1,3-thiazol-3-ium salts,
3-methyl-2-(2-{3-methyl-4-[methyl({3-[methyl({2-methyl-4-[2-(3-methyl-1,3-thiazol-3-ium-2-yl)diazen-1-yl]phenyl}amino)propyl]amino}phenyl)diazen-1-yl]-1,3-thiazol-3-ium salts,
3-methyl-2-(2-{3-methyl-4-[ethyl({3-[ethyl({2-methyl-4-[2-(3-methyl-1,3-thiazol-3-ium-2-yl)diazen-1-yl]phenyl })amino]propyl })amino]phenyl}diazen-1-yl)-1,3-thiazol-3-ium salts,
3-methyl-2-(2-{2-methyl-4-[methyl({3[methyl({3-methyl-4-[2-(3-methyl-1,3-thiazol-3-ium-2-yl)diazen-1-yl]phenyl })amino]propyl })amino]phenyl}diazen-1-yl)-1,3-thiazol-3-ium salts,
3-methyl-2-(2-{2-methyl-4-[ethyl({3-[ethyl({3-methyl-4-[2-(3-methyl-1,3-thiazol-3-ium-2-yl)diazen-1-yl]phenyl })amino]propyl })amino]phenyl}diazen-1-yl)-1,3-thiazol-3-ium salts,
3-methyl-2-(2-{3-methyl-4-[methyl({4-[methyl({2-methyl-4-[2-(3-methyl-1,3-thiazol-3-ium-2-yl)diazen-1-yl]phenyl})amino]butyl })amino]phenyl}diazen-1-yl)-1,3-thiazol-3-ium salts,
3-methyl-2-(2-{2-methyl-4-[methyl({4-[methyl({3-methyl-4-[2-(3-methyl-1,3-thiazol-3-ium-2-yl)diazen-1-yl]phenyl})amino]butyl})amino]phenyl}diazen-1-yl)-1,3-thiazol-3-ium salts,
3-methyl-2-(2-{3-methyl-4-[methyl({5-[methyl({2-methyl-4-[2-(3-methyl-1,3-thiazol-3-ium-2-yl)diazen-1-yl]phenyl})amino]pentyl})amino]phenyl}diazen-1-yl)-1,3-thiazol-3-ium salts, 3-methyl-2-(2-{2-methyl-4-[methyl({5-[methyl({3-methyl-4-[2-(3-methyl-1,3-thiazol-3-ium-2-yl)diazen-1-yl]phenyl})amino]pentyl})amino]phenyl}diazen-1-yl)-1,3-thiazol-3-ium salts, 2-[2-(3-methoxy-4-{[3-({2-methoxy-4-[2-(3-methyl-1,3-thiazol-3-ium-2-yl)diazen-1-yl]phenyl}amino)propyl]amino}phenyl)diazen-1-yl]-3-methyl-1,3-thiazol-3-ium salts, 2-[2-(2-methoxy-4-{[3-({3-methoxy-4-[2-(3-methyl-1,3-thiazol-3-ium-2-yl)diazen-1-yl]phenyl}amino)propyl]amino}phenyl)diazen-1-yl]-3-methyl-1,3-thiazol-3-ium salts, 2-[2-(3-methoxy-4-{[4-({2-methoxy-4-[2-(3-methyl-1,3-thiazol-3-ium-2-yl)diazen-1-yl]phenyl}amino)butyl]amino}phenyl)diazen-1-yl]-3-methyl-1,3-thiazol-3-ium salts, 2-[2-(2-methoxy-4-{[4-({3-methoxy-4-[2-(3-methyl-1,3-thiazol-3-ium-2-yl)diazen-1-yl]phenyl}amino)butyl]amino}phenyl)diazen-1-yl]-3-methyl-1,3-thiazol-3-ium salts, 2-[2-(3-methoxy-4-{[5-({2-methoxy-4-[2-(3-methyl-1,3-thiazol-3-ium-2-yl)diazen-1-yl]phenyl}amino)pentyl]amino}phenyl)diazen-1-yl]-3-methyl-1,3-thiazol-3-ium salts, 2-[2-(2-methoxy-4-{[5-({3-methoxy-4-[2-(3-methyl-1,3-thiazol-3-ium-2-yl)diazen-1-yl]phenyl}amino)pentyl]amino}phenyl)diazen-1-yl]-3-methyl-1,3-thiazol-3-ium salts, 2-[2-(3-methoxy-4-{[3-({2-methoxy-4-[2-(3-methyl-1,3-thiazol-3-ium-2-yl)diazen-1-yl]phenyl}(methyl)amino)propyl](methyl)amino}phenyl)diazen-1-yl]-3-methyl-1,3-thiazol-3-ium salts, 2-[2-(2-methoxy-4-{[3-({3-methoxy-4-[2-(3-methyl-1,3-thiazol-3-ium-2-yl)diazen-1-yl]phenyl}(methyl)amino)propyl](methyl)amino}phenyl)diazen-1-yl]-3-methyl-1,3-thiazol-3-ium salts, 2-[2-(3-methoxy-4-{[4-({2-methoxy-4-[2-(3-methyl-1,3-thiazol-3-ium-2-yl)diazen-1-yl]phenyl}(methyl)amino)butyl]methyl)amino}phenyl)diazen-1-yl]-3-methyl-1,3-thiazol-3-ium salts, 2-[2-(2-methoxy-4-{[4-({3-methoxy-4-[2-(3-methyl-1,3-thiazol-3-ium-2-yl)diazen-1-yl]phenyl}(methyl)amino)butyl]methyl)amino}phenyl)diazen-1-yl]-3-methyl-1,3-thiazol-3-ium salts, 2-[2-(3-methoxy-4-{[5-({2-methoxy-4-[2-(3-methyl-1,3-thiazol-3-ium-2-yl)diazen-1-yl]phenyl}(methyl)amino)pentyl]methyl)amino}phenyl)diazen-1-yl]-3-methyl-1,3-thiazol-3-ium salts, 2-[2-(2-methoxy-4-{[5-({3-methoxy-4-[2-(3-methyl-1,3-thiazol-3-ium-2-yl)diazen-1-yl]phenyl}(methyl)amino)pentyl]methyl)amino}phenyl)diazen-1-yl]-3-methyl-1,3-thiazol-3-ium salts, 5-[2-(4-{[3-({4-[2-(1,4-dimethyl-1H-1,2,4-triazol-4-ium-5-yl)diazen-1-yl]-2-methylphenyl}amino)propyl]amino}-3-methylphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-3-methylphenyl}amino)propyl]amino}-2-methylphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-2-methylphenyl}amino)butyl]amino}-3-methylphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-3-methylphenyl}amino)butyl]amino}-2-methylphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-2-methylphenyl}amino)pentyl]amino}-3-methylphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-3-methylphenyl}amino)pentyl]amino}-2-methylphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-2-methylphenyl}(methyl)amino)propyl](methyl)amino}-3-methylphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-3-methylphenyl}(methyl)amino)propyl](methyl)amino}-2-methylphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-2-methylphenyl}(methyl)amino)butyl](methyl)amino}-3-methylphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-3-methylphenyl}(methyl)amino)butyl](methyl)amino}-2-methylphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-2-methylphenyl}(methyl)amino)pentyl]methyl)amino}-3-methylphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-3-methylphenyl}(methyl)amino)pentyl]methyl)amino}-2-methylphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-2-methoxyphenyl}amino)propyl]amino}-3-methoxyphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-3-methoxyphenyl}amino)propyl]amino}-2-methoxyphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-2-methoxyphenyl}amino)butyl]amino}-3-methoxyphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-3-ethoxyphenyl}amino)butyl]amino}-2-methoxyphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-2-methoxyphenyl}amino)pentyl]amino}-3-methoxyphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-3-methoxyphenyl}amino)pentyl]amino}-2-methoxyphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-2-methoxyphenyl}(methyl)amino)propyl]methyl)amino}-3-methoxyphenyl)diazen-1-yl]-1,4-dimethyl-1H-1,2,4-triazol-4-ium salts, 5-[2-(4-{[3-({4-[2-(1,4-dimethyl-1H-1,2,4-triazol-4-ium-5-yl)diazen-1-yl]-3-methoxyphenyl}(methyl)amino)propyl]methyl)amino}-2-methoxyphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-2-methoxyphenyl }(methyl)amino)butyl](methyl)amino}-3-methoxyphenyl)diazen-1-yl]-1,4-dimethyl-1H-1,2,4-triazol-4-ium salts, 5-[2-(4-{[4-({4-[2-(1,4-dimethyl-1H-1,2,4-triazol-4-ium-5-yl)diazen-1-yl]-3-methoxyphenyl }(methyl)amino)butyl](methyl)amino}-2-methoxyphenyl)diazen-1-yl]-1,4-dimethyl-1H-1,2,4-triazol-4-ium salts, 5-[2-(4-{[5-({4-[2-(1,4-dimethyl-1H-1,2,4-triazol-4-ium-5-yl)diazen-1-yl]-2-methoxyphenyl }(methyl)amino)pentyl](methyl)amino}-3-methoxyphenyl)diazen-1-yl]-1,4-dimethyl-1H-1,2,4-triazol-4-ium salts, and 5-[2-(4-{[5-({4-[2-(1,4-dimethyl-1H-1,2,4-triazol-4-ium-5-yl)diazen-1-yl]-3-methoxyphenyl }(methyl)amino)pentyl](methyl)amino}-2-methoxyphenyl)diazen-1-yl]-1,4-dimethyl-1H-1,2,4-triazol-4-ium salts.

6. The agent as claimed in claim 1, wherein with respect to the total weight of the agent, the agent comprises one or more direct dyes (a) with formula (I) in a total quantity of about 0.01% to about 4.5% by weight.

7. The agent as claimed in claim 1, wherein with respect to the total weight of the agent, the agent comprises about 0.5% to about 12.5% by weight of hydrogen peroxide.

8. The agent as claimed in claim 1, wherein the agent comprises at least one $SiO_2$ compound from the group formed by silicas, silicates, water glasses and/or alkali metal silicates.

9. The agent as claimed in claim 1, wherein the agent further comprises at least one further cationic direct dye which is different from the dyes with formula (I).

10. The agent as claimed in claim 1, wherein the agent further comprises Basic Orange 31 and/or Basic Red 51.

11. The agent as claimed in claim 1, wherein with respect to the total weight of the agent, the agent comprises one or more direct dyes (a) with formula (I) in a total quantity of about 0.05% to about 2.8% by weight.

12. The agent as claimed in claim 1, wherein with respect to the total weight of the agent, the agent comprises one or more direct dyes (a) with formula (I) in a total quantity of about 0.1% to about 2.2% by weight.

13. The agent as claimed in claim 1, wherein with respect to the total weight of the agent, the agent comprises one or more direct dyes (a) with formula (I) in a total quantity of about 0.2% to about 1.2% by weight.

14. The agent as claimed in claim 1, wherein with respect to the total weight of the agent, the agent comprises about 2.5% to about 10% by weight of hydrogen peroxide.

15. The agent as claimed in claim 1, wherein with respect to the total weight of the agent, the agent comprises about 4.0% to about 9.0% by weight of hydrogen peroxide.

16. The agent as claimed in claim 1, wherein the agent comprises at least one persulfate selected from the group consisting of ammonium peroxydisulfate, potassium peroxodisulfate, or sodium peroxydisulfate.

17. The agent as claimed in claim 1, wherein, with respect to the total weight of the agent, the agent comprises one or more persulfates selected from the group consisting of ammonium peroxydisulfate, potassium peroxodisulfate or sodium peroxydisulfate in a total amount of from about 0.5 to about 20 wt.-%.

18. The agent as claimed in claim 1, wherein, with respect to the total weight of the agent, the agent comprises one or more persulfates selected from the group consisting of ammonium peroxydisulfate, potassium peroxodisulfate or sodium peroxydisulfate in a total amount of from about 1.0 to about 12.5 wt.-%.

19. The agent as claimed in claim 1, wherein, with respect to the total weight of the agent, the agent comprises one or more persulfates selected from the group consisting of ammonium peroxydisulfate, potassium peroxodisulfate or sodium peroxydisulfate in a total amount of from about 2.5 to about 10 wt.-%.

20. The agent as claimed in claim 1, wherein with respect to the total weight of the agent, the agent comprises:
- about 0.2% to about 13.5% by weight of ammonium peroxodisulphate,
- about 0.5% to about 4.5% by weight of potassium peroxodisulphate, and
- about 0.2% to about 1.8% by weight by weight of sodium peroxodisulphate.

\* \* \* \* \*